(12) United States Patent
Egawa et al.

(10) Patent No.: US 7,722,814 B2
(45) Date of Patent: May 25, 2010

(54) MEASURING INSTRUMENT USING CENTRIFUGAL FORCE

(75) Inventors: Shunji Egawa, Saitama (JP); Yasuo Tsukahara, Osaka (JP)

(73) Assignee: Citizen Holdings Co., Ltd., Tokyo (JP)

( * ) Notice: Subject to any disclaimer, the term of this patent is extended or adjusted under 35 U.S.C. 154(b) by 703 days.

(21) Appl. No.: 11/691,821

(22) Filed: Mar. 27, 2007

(65) Prior Publication Data
US 2007/0221497 A1    Sep. 27, 2007

(30) Foreign Application Priority Data
Mar. 27, 2006  (JP) .............................. 2006-085779

(51) Int. Cl.
*G01N 9/30* (2006.01)
(52) U.S. Cl. ........................................ 422/72
(58) Field of Classification Search .................... 422/72
See application file for complete search history.

(56) References Cited
FOREIGN PATENT DOCUMENTS

| JP | 2002-310973 A | 10/2002 |
| JP | 2003-107080 A | 4/2003 |
| JP | 2004-109082 A | 4/2004 |

*Primary Examiner*—Walter D Griffin
*Assistant Examiner*—Bobby Ramdhanie
(74) *Attorney, Agent, or Firm*—Westerman, Hattori, Daniels & Adrian, LLP

(57) ABSTRACT

Both application of centrifugal force to a biosensor and electrical connection with an electrode of the biosensor can be achieved with a simple structure. The electrode of the biosensor and a measuring part are connected without aligning a rotational position of the rotary table. The centrifugal measuring apparatus 1 is provided with a rotary table 2 that is driven by a motor, a retainer 3 to hold a biosensor accommodating a sample inside on the rotary table, an urged contact part 4 that establishes electrical connection with the electrode of the biosensor in such a manner as being elastically biased to abut against the electrode, a measuring part 8 that measures a signal from the electrode of the biosensor, and a connector part 7 that selectively establishes electrical connection between the urged contact part 4 and the measuring part 8. A contact having a circular shape is utilized to establish electrical connection between the rotary table 2 on which the biosensor 20 is mounted and the fixture side, thereby enabling an electrical connection therebetween irrespective of a position of the biosensor on the rotary table, when the rotary table is stopped.

20 Claims, 20 Drawing Sheets

MOUNTING

CENTRIFUGAL SEPARATION

ENERGIZATION AND MEASUREMENT

ENERGIZATION AND MEASUREMENT

MOUNTING

CENTRIFUGAL SEPARATION

STOP.→ ALIGNMENT

ENERGIZATION AND MEASUREMENT

MEASURING INSTRUMENT USING CENTRIFUGAL FORCE

BACKGROUND OF THE INVENTION

1. Field of the Invention

The present invention relates to a measuring apparatus that applies centrifugal force to a sample for carrying out a measurement. More particularly, it relates to a measuring apparatus that is applicable to a measuring instrument used in a blood test and the like, for example, which centrifugally separates a blood sample and analyzes blood components being obtained.

2. Description of the Related Art

In a blood test in the field of clinical diagnosis, a disease state of a subject, a recovery condition after treatment, and the like are grasped, by means of analyzing a specific component of the blood being collected. Generally, in the blood test as described above, the blood being collected is separated by component, and analysis is conducted only on the component containing a substance to be analyzed. In many cases, a serum component is considered as a target item for checking in a biochemical examination of blood.

In measuring and analyzing a sample such as blood, there is known a measuring apparatus that centrifugally separates components contained in the sample by using centrifugal force, so as to measure a component being separated. For instance, the blood being collected is subjected to a centrifugal separation, to obtain blood serum and the like by separating erythrocyte, leucocyte, lymphocyte, platelet, and blood coagulation factors, and the blood serum and the like are each taken into test tubes. Then, with respect to each, concentration of pH, oxygen, carbon dioxide, and the like, are measured by a chemical sensor. In addition, a test reagent such as enzyme is injected and an emission reaction with a substrate in the blood serum is subjected to spectroscopy or absorption spectroscopy (for example, see Japanese Unexamined Patent Application Publication No. 2003-107080, paragraphs 0002 and 0020, hereinafter, referred to as "patent document 1").

In addition to the above method where the component centrifugally separated is injected in each test tube and the analysis is conducted therein, there is also known a technique for the blood analysis, which uses an apparatus called a biosensor. This biosensor has a structure to collect a sample and also transport the sample being collected to an analysis part. Centrifugal force is applied to the biosensor while keeping the sample inside, thereby transporting the sample being collected to the analysis part within the biosensor, and further the sample is subjected to the centrifugal separation within the analysis part. Furthermore, as a way of example, a reagent may be provided within the analysis part, enabling an analysis by reaction of a component with the reagent.

As a representative example of testing equipment used for examination at home, a device for SMBG (Self Monitoring of Blood Glucose) has been developed, which measures glucose concentration in blood (blood glucose level). In the examination employing the SMBG device broadly used these days, the subject oneself stabs a fingertip or an arm with paracentesis needle, and a small amount of blood sample having bled is utilized.

To be exact, the blood glucose level indicates glucose concentrations in the serum. The most common method for measuring the glucose concentrations is the one which utilizes an enzyme electrode. In this measuring method, a whole blood sample being collected is fed into a biosensor, and it is subjected to a measurement. The biosensor has an enzyme reaction layer inside. According to an amperometric measuring method, the enzyme reaction layer measures a current in accordance with the glucose concentration in the serum without hemolyzing the blood cell. In this measuring method, the concentration of a particular component in the serum is measured without separating the blood cell component.

Japanese Unexamined Patent Application Publication No. 2002-310973, pages 6 to 8, hereinafter, referred to as "patent document 2", discloses an electrochemical biosensor as a simple instrument for measuring blood glucose level, which measures the glucose concentration in the whole blood sample collected from human. This biosensor is provided with a suction port for sucking a sample, and when the whole blood sample as a sample is provided to this suction port, the whole blood sample is sucked into a suction cavity called as a capillary fill chamber, by means of capillary phenomenon. This sucking into the suction cavity is performed by letting the air in the suction cavity out of a vent hole which is formed in the recesses of the suction cavity.

A working electrode and a counter electrode are arranged in this suction cavity. These electrodes obtain a measured current value being correlated with the glucose concentration, in a condition that the whole blood sample includes a blood cell component. Based on this measured current value, the blood glucose level can be measured easily.

Japanese Unexamined Patent Application Publication No. 2004-109082, pages 6 to 9, hereinafter, referred to as "patent document 3", discloses a biosensor for blood analysis which performs a plasma separation by centrifugal operation. A flow channel of the biosensor for blood analysis is provided with a portion where a blood cell component is accumulated in the centrifugal direction upon centrifugal separation. With the centrifugal separation, the blood cell component is accumulated on the bottom, and a plasma component is separated as supernatant. In order to introduce the whole blood sample obtained from the subject as a sample, this biosensor is provided with an external pump at an outlet port, and the whole blood sample is suctioned by the suction negative pressure from the blood suction port. Similarly, it is also configured such that the plasma component after the centrifugal separation is transferred to an analytical position by the suction negative pressure from the external pump. In addition, the blood analyzer disclosed in the patent document 1 includes a configuration to apply centrifugal force by rotating the biosensor having an electrode, and the electrode of the biosensor is brought into electrical contact with a point of contact.

In the blood analyzer disclosed in the patent document 1 as described above, the biosensor is mounted on a rotary table, and centrifugal force is applied to the biosensor by turning this rotary table. There is also a configuration that an opening is provided on the rotary table to establish electrical connection with the electrode of the biosensor, and a contact for measurement is made to move up and down through this opening part.

In this configuration, when the rotary table is to be rotated, the contact for measurement is moved down, and centrifugal force can be applied to the biosensor by turning the rotary table without an interference with the contact. When the measurement is performed, the rotary table is brought to a halt, then, the contact for measurement is raised by passing through the aforementioned opening, and electrical connection is established with the electrode of the biosensor.

According to this configuration, both application of centrifugal force and measurement via the electrode, targeting a sample taken into the biosensor, can be performed within one biosensor. Therefore, an operation to move the sample is unnecessary, thereby achieving a configuration suitable for an automatic analysis.

In the measuring device using centrifugal force, electrical connection between the contact for measurement and the electrode of biosensor is necessary, when the measurement is carried out. Generally, when the rotary table is stopped having been rotating at a high speed, without any control, a position where the rotary table being stopped is random in the circumferential direction. Therefore, in the above configuration for measurement, generally, the stop position of the contact for measurement is not always opposed to the electrode of the biosensor. It is thus required to align the contact for measurement with the position being opposed to the electrode of the biosensor.

FIG. 20A to FIG. 20D are illustrations to explain a positional relationship between the contact for measurement and the electrode of the biosensor in the conventional measuring device utilizing centrifugal force. FIG. 20A illustrates that the biosensor 111 is being mounted on the rotary table 102. The biosensor 110 is fixed on and held by a retainer 103 that is provided on the board face of the rotary table 102. The biosensor 110 receives centrifugal force generated by turning the rotary table 102 rotatably supported by the rotary shaft 101, and the sample stored inside is centrifugally separated (FIG. 20B). After the centrifugal separation is finished, the turning of the rotary table 102 is brought to a halt. Then, the rotational position of the rotary table is adjusted for alignment, whereby the electrode 111 of the biosensor 110 is electrically connected to the contact for measurement 104 (FIG. 20C). In the state where the electrode 111 of the biosensor 110 and the contact for measurement 104 are electrically connected, the electrode 111 is energized and simultaneously a measured current is checked (FIG. 20D). In order to establish the electrical connection between the electrode 111 of the biosensor 110 and the contact for measurement 114, alignment is necessary at the time of halt as shown in FIG. 20C.

As a way of example to align the contact for measurement with a position opposed to the electrode of the biosensor, there is a configuration to install a controller to control the rotation of the rotary table, or a configuration to employ a stepping motor.

However, installation of such controller to control the rotation may be a factor that increases the cost of the device. This rise in cost by installing the controller may become more pronounced, as a rotating speed of the rotary table is set to be higher. If the stepping motor is employed, it is possible to control the stop position, but the rotating speed is hardly set to be high. Therefore, it is not applicable when large centrifugal force is to be applied.

In order to address the problems as described above, an object of the present invention is to provide a simple configuration which both applies centrifugal force to the biosensor and establishes electrical connection with the electrode of the biosensor. The present invention further aims at establishing connection between the electrode of the biosensor and the measuring part, without an alignment of the rotational position of the rotary table.

SUMMARY OF THE INVENTION

A centrifugal measuring apparatus according to the present invention uses a circular contact to establish electrical connection between a rotary table side where a biosensor is mounted, and a fixture side. When the rotary table is brought to a halt, the configuration above enables the electrical connection between the rotary table side and the fixture side, irrespective of a position of the biosensor mounted on the rotary table. Accordingly, both application of centrifugal force to the biosensor and electrical connection with the electrode of the biosensor can be achieved with a simple structure.

A first embodiment of the centrifugal measuring apparatus according to an aspect of the present invention is directed to a configuration in which a circular contact is provided on the rotary table side to establish electrical connection between the rotary table side and the fixture side. A second embodiment of the centrifugal measuring apparatus according to an aspect of the present invention is directed to a configuration in which the circular contact is provided on the fixture side.

The first embodiment of the centrifugal measuring apparatus according to an aspect the present invention includes a rotary table that is driven by a motor, a retainer that holds on the rotary table a biosensor accommodating a sample inside, an urged contact part that abuts against an electrode of the biosensor with a biased force to establish electrical connection, a measuring part that measures a signal from the electrode of the biosensor, and a connector part that selectively establishes the electrical connection between the urged contact and the measuring part.

In the first embodiment, a circular contact which is electrically connected with the urged contact part is provided along the circumference of the rotary table, or along the circumference of a rotary shaft of a rotor that is placed coaxially with the rotary table. Furthermore, a connector part provided on the fixture side has a movable contact that is capable of freely coming into contact with or separating from the circular contact at any position on the circle of the circular contact.

In the first embodiment, when the circular contact described above is brought into contact with the movable contact, connection between the biosensor and the measuring part externally provided can be established irrespective of a stop position of the rotary table. According to the connection between the circular contact and the movable contact, the biosensor is energized and a measured signal from the electrode of the biosensor is transmitted to the measuring part.

When the rotary table is rotated, the connector part moves the movable contact to be separated from the circular contact. In this separated condition, the rotary table is allowed to rotate at high speed without any influence of contact with the connector part. By rotating the rotary table at high speed, large centrifugal force is applied to the biosensor mounted on the rotary table. This centrifugal force enables the sample within the biosensor to be subjected to centrifugal separation.

On the other hand, when the rotary table is brought to a halt, the connector part moves the movable contact to abut against the circular contact, or the circular contact is made to abut against the movable contact. According to this abutment therebetween, the movable contact and the circular contact are brought into contact with each other, and the biosensor is energized and a measured signal from the electrode of the biosensor is transmitted to the measuring part.

In establishing a contact between the movable contact and the circular contact, the circular contact is provided on the rotating member side, such as the rotary table or the rotor provided coaxially with the rotary table. Therefore, the point of contact can be positioned at any place on the circle of the circular contact. With this configuration, when the rotary table stops at any rotational position with respect to the measuring part side, the movable contact is allowed to come into contact with the circular contact to establish electrical connection, irrespective of the stop position. Therefore, it is not necessary to adjust the stop position of the rotary table for the alignment with the contact position.

It is to be noted that the biosensor applied to the centrifugal measuring apparatus according to an aspect of the present invention is a biosensor that is provided with a suction cavity to suck a certain amount of sample by capillary phenomenon, for example.

The circular contact provided in the first embodiment of the present invention may be configured to include multiple circular contacts placed at positions each displaced in the axial direction, on either the outer circumferential surface or the inner circumferential surface of a cylindrical body or a cone, which is arranged coaxially with the rotary table. Alternatively, the circular contact may be provided on the board face of the rotary table, and multiple circular contacts may be placed, respectively having different diameters concentrically.

The urged contact part provided in the retainer is electrically connected with the circular contact by wiring such as flexible wiring or printed wiring, which is placed on the rotary table, as a way of example.

The movable contact includes an elastic contact such as a contact spring, and a moving mechanism that enables the elastic contact to move freely towards the circular contact.

When connection is to be established, the moving mechanism moves the elastic contact to approach the circular contact and abut thereto. Upon this abutment, the elastic contact comes into contact with the circular contact using the elasticity of the elastic contact. Therefore, favorable contact condition can be maintained, as well as a positional error is compensated. On the other hand, when connection is not established, the moving mechanism moves the elastic contact in a direction separating from the circular contact.

The second embodiment of the centrifugal measuring apparatus according to the present invention includes, similar to the first embodiment, a rotary table that is driven by a motor, a retainer that holds a biosensor on the rotary table, an urged contact part that abuts against an electrode of the biosensor with a biased force to establish electrical connection, a measuring part that measures a signal from the electrode of the biosensor, and a connector part that selectively establishes the electrical connection between the urged contact and the measuring part.

In the second embodiment, a point of contact electrically connected to the urged contact part is provided on a circle along the circumference of the rotary shaft of the rotary table. The connector part is provided with a circular movable contact that freely comes into contact with and separates from the point of contact on the rotary table at any circular position.

In the second embodiment, since the point of contact as described above is brought into contact with the circular movable contact, the biosensor is allowed to be connected with the measuring part externally provided, irrespective of the stop position of the rotary table. The biosensor is energized via the connection between the point of contact and the circular movable contact, as well as a measured signal from the electrode of the biosensor is transmitted to the measuring part.

When the rotary table is rotated, the connector part moves so that the point of contact and the circular movable contact separate from each other. In this separated condition, the rotary table is allowed to rotate at high speed without any influence of contact with the connector part. By rotating the rotary table at high speed, large centrifugal force is applied to the biosensor mounted on the rotary table. This centrifugal force enables the sample within the biosensor to be subjected to centrifugal separation.

On the other hand, when the rotary table is brought to a halt, the connector part makes the point of contact to abut against the circular movable contact, or the circular movable contact is made to abut against the point of contact. According to this abutment therebetween, the point of contact and the circular movable contact are brought into contact with each other, and the biosensor is energized and a measured signal from the electrode of the biosensor is transmitted to the measuring part.

In establishing a contact between the point of contact and the circular movable contact, the circular movable contact is provided on a fixture side member. Therefore, a contact position of the rotary table or the rotor coaxially provided can be set at any point on a circle of the circular movable contact. With this configuration, when the rotary table stops at any rotational position with respect to the measuring part side, the point of contact is allowed to come into contact with the circular movable contact to establish electrical connection, irrespective of the stop position. Therefore, it is not necessary to adjust the stop position of the rotary table for the alignment with the contact position.

In the second embodiment, multiple circular movable contacts are provided on a surface of a member opposed to the rotary table, respectively with different diameters concentrically, the member having a function of freely coming into contact with or separating from the rotary table, in such a manner as opposed to the rotary table. The circular movable contacts are also provided with a moving mechanism that is movable towards the point of contact on the rotary table. This moving mechanism allows the circular movable contacts to come into contact with and separate from the point of contact on the rotary table. A solenoid may constitute the moving mechanism.

In both the first and second embodiments of the present invention, the connector part energizes the electrode of the biosensor and transmits a measured signal from the electrode to the measuring part, via the circular contact. Furthermore, the moving mechanism may include a solenoid. The retainer may be provided with a concave part to store the biosensor on the board face of the rotary table, and the urged contact part may be provided on the bottom or on the side surface of the concave part. The urged contact part may include a contact pin that comes into contact with the electrode, and a spring to elastically urge the contact pin in a predetermined direction. The rotary table may be driven by a DC motor.

Here, the contact pin of the urged contact part is not necessarily provided with the spring. For example, another configuration is possible such as generating a contact pressure with the contact pin, when the biosensor is fixed.

According to the centrifugal measuring apparatus of the present invention, even with a simple structure, the electrode of the biosensor can be connected with the measuring part without aligning the rotational position of the rotary table. In addition, application of centrifugal force to the biosensor can be performed with this simple structure.

DETAILED DESCRIPTION OF THE INVENTION

Figure 9:
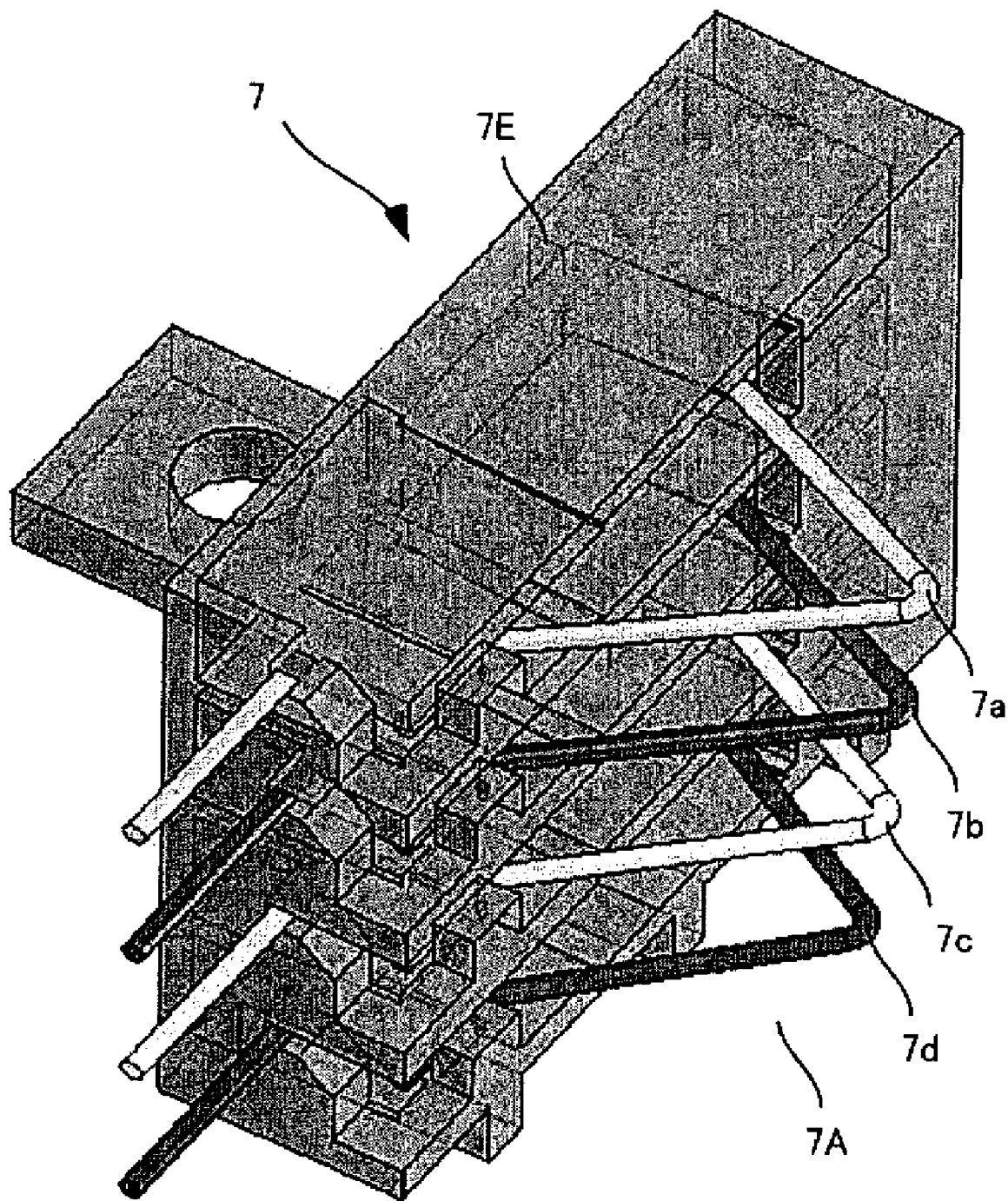
FIG. 9 is a schematic illustration showing the connector part of a configuration example of the centrifugal measuring apparatus according to the first embodiment of the present invention.
Figure 10:
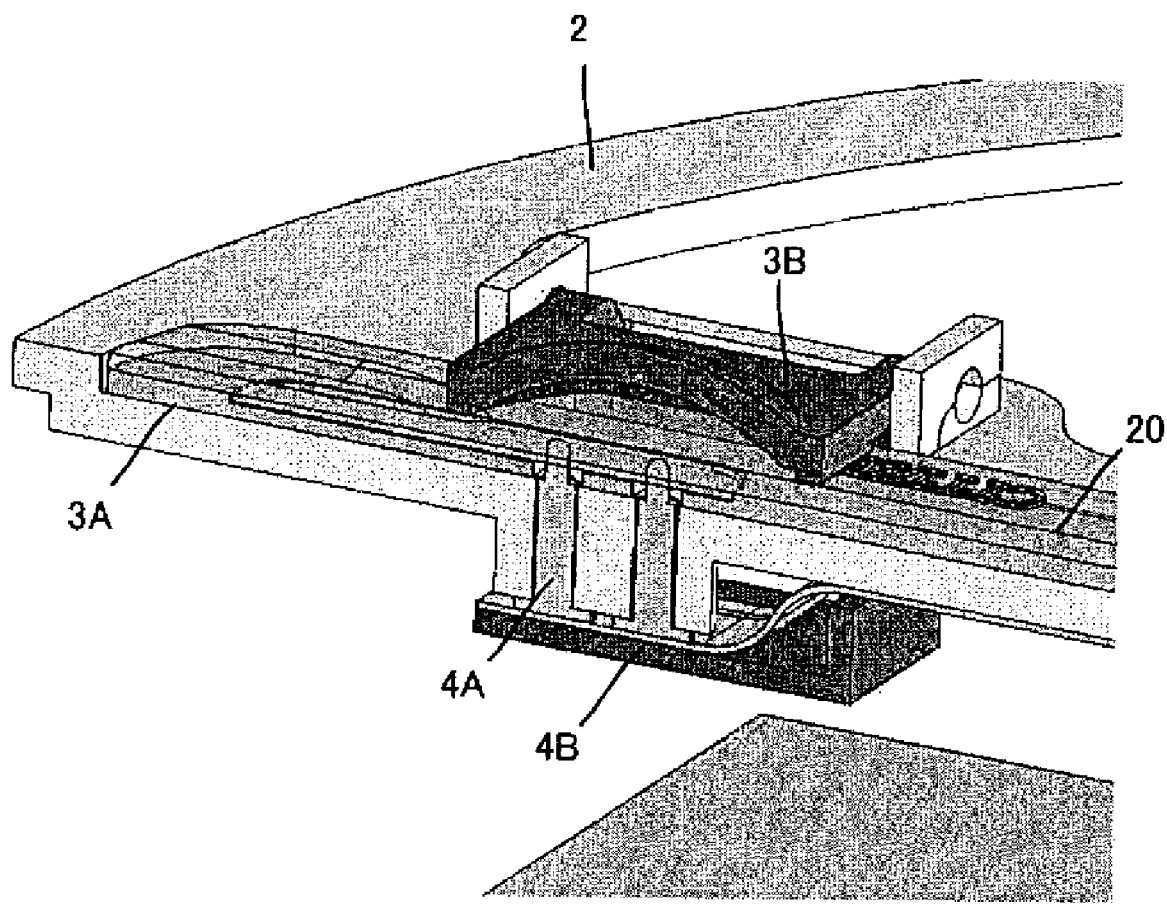
FIG. 10 is a cross sectional view showing the retainer and the urged contact part of a configuration example of the centrifugal measuring apparatus according to the first embodiment of the present invention.
Figure 11:
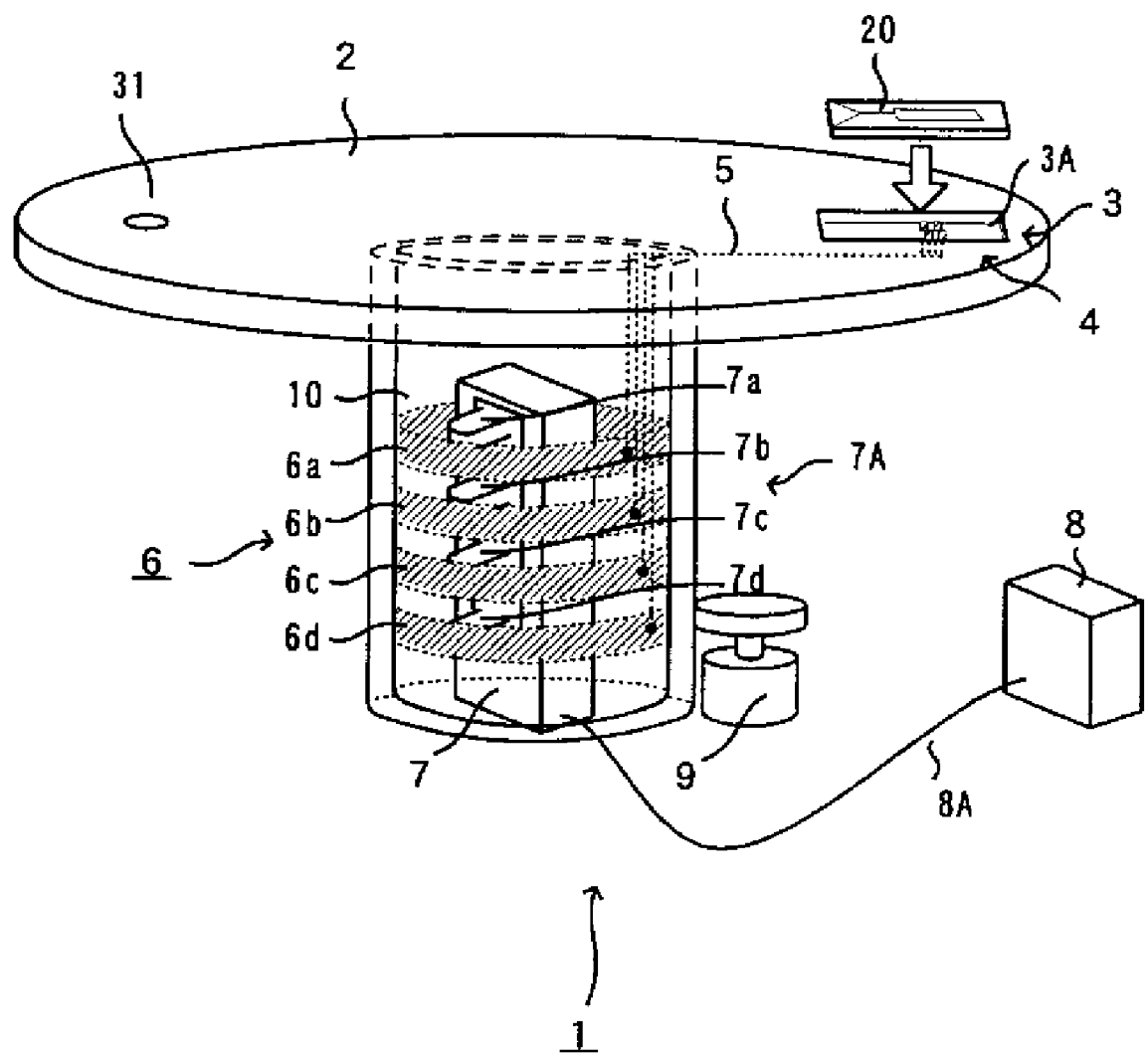
FIG. 11 is an illustration to explain a second configuration example of the centrifugal measuring apparatus according to the first embodiment of the present invention.

Firstly, a first embodiment of the centrifugal measuring apparatus according to an aspect of the present invention will be explained. Here, it is to be noted that FIG. 1 to FIG. 10 illustrate a first configuration example of the first embodiment, FIG. 11 to FIG. 12C illustrate a second configuration example of the first embodiment, and FIG. 13 to FIG. 15C illustrate a third configuration of the first embodiment.

Figure 1:
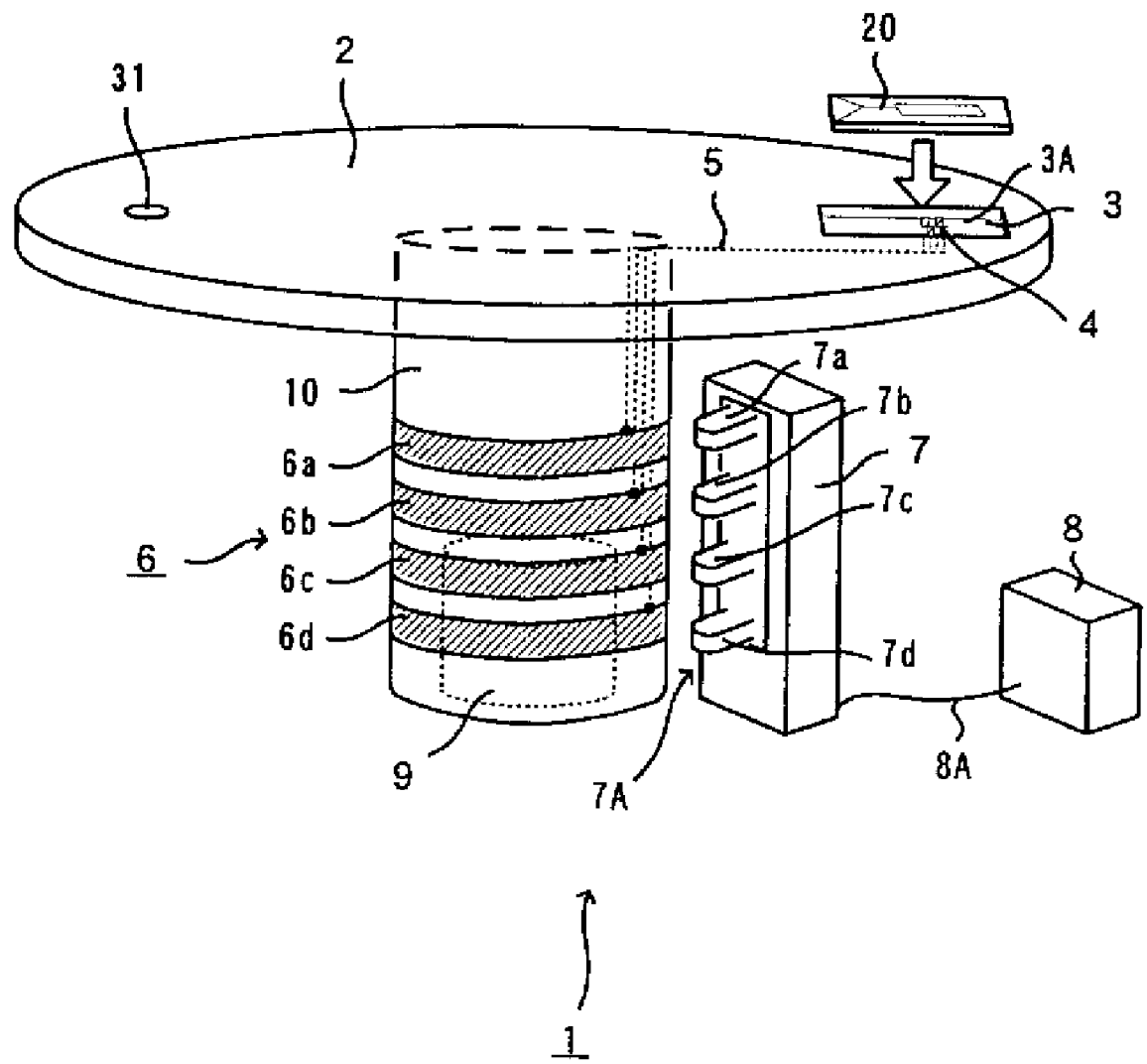
FIG. 1 is a schematic illustration to explain a first configuration example of a centrifugal measuring apparatus according to a first embodiment of the present invention.

FIG. 1 is a schematic illustration to explain the first configuration example of the centrifugal measuring apparatus according to the first embodiment of the present invention.

The centrifugal measuring apparatus 1 is provided with a rotary table 2 that is rotationally driven by a DC motor 9 as a way of example, a retainer 3 to hold a biosensor 20 on the rotary table 2, an urged contact part 4 that is elastically biased to abut against an electrode (not illustrated in this Figure) provided on the biosensor 20 and establishes electrical connection with the electrode, a measuring part 8 that measures a signal from the electrode of the biosensor 20, and a connector part 7 that selectively establishes electrical connection between the urged contact part 4 and the measuring part 8.

The DC motor 9 rotates the rotary table 2 at high speed, thereby applying centrifugal force to the biosensor 20 held by the retainer 3 of the rotary table 2. The biosensor 20 accommodates a sample inside. When centrifugal force is applied to the biosensor 20, the sample being collected is moved to the interior of an analytical cavity, and further the sample is subjected to the centrifugal separation within the analytical cavity. In addition, an enzyme reaction layer is provided within the analysis cavity, and a component being centrifugally separated is subjected to an electrochemical measurement. The electrochemical measurement is performed by energizing the electrode provided in the biosensor 20, and simultaneously deriving a measured signal detected in the electrode to the measuring part 8 that is prepared externally. It is further possible to place a counter balance 31 on the rotary table 2, at a diametrically opposed location to the retainer 3 via the central axis.

The urged contact part 4 provided on the rotary table 2 is electrically connected to the electrode of the biosensor 20 held by the retainer 3, by bringing a contact pin into contact with the electrode.

On the other hand, a circular contact part 6 is placed on the circumference of the rotor 10 that is coaxial with the rotary table 2. The circular contact part 6 may be provided by placing multiple circular contacts 6a to 6d with a predetermined distance therebetween in the axial direction of the rotor 10. The number of the circular contacts 6a to 6d may be equal to the number of the electrodes of the biosensor 20 and the contacts of the urged contact part 4, whereby electrical connection is established between the points of contact of the urged contact part 4 and the circular contacts, respectively. The circular contact part 6 is electrically connected to the urged contact part 4 via wiring 5 such as flexible wiring and printed wiring placed on the rotary table 2 and the rotor 10. The rotary table 2 and the rotor 10 are rotated integrally, along with the rotation of the motor 9.

The number of the circular contacts 6a to 6d is determined according to the number of the points of contact in the urged contact part 4. The number of the points of contact in the urged contact part 4 is determined according to the number of points of contact in the biosensor 20. It is to be noted that the number of the point of contact in the urged contact part 4 does not necessarily correspond to the number of the point of contact in the biosensor 20. If a ground or another contact is added to the urged contact part 4, the number of the points of contact in the urged contact part 4 will be equal to the number obtained by adding the number of these extra contacts to the number of the point of contact in the biosensor 20.

The connector part 7 is provided with a movable contact part 7A having multiple contacts. The movable contact part 7A is capable of freely coming into contact with and separating from the circular contact part 6, and includes movable contacts 7a to 7d that are allowed to contact respectively with the circular contacts 6a to 6d. The movable contacts 7a to 7d are configured to be movable by using a solenoid or a motor (not illustrated). By driving the solenoid or the motor, the movable contacts 7a to 7d are allowed to abut against the circular contacts 6a to 6d, thereby establishing electrical connection, or releasing the electrical connection by separating the movable contacts from the circular contacts.

The connector part 7 is connected to the measuring part 8. The electrode provided in the biosensor 20 is energized, via the connector part 7, from the measuring part 8 or a power source not illustrated, and a measured signal from the electrode of the biosensor 20 is transmitted to the measuring part 8 via the connector part 7. The rotary table 2 and the rotor 10 are turned by the motor 9, whereas the connector part and the measuring part 8 are fixed. It is to be noted here, as a way of example, the connector part 7 and the measuring part 8 may be connected via wiring 8A.

The circular contact part 6 and the urged contact part 4 are electrically connected via the wiring 5 provided on the rotary table 2 and the rotor 10. Therefore, even in the case where the rotary table 2 and the rotor 10 are turned and a rotational position is changed, electrical relationship among the circular contact part 6, the urged contact part 4, and the contact part 7 are unchanged, since there is only a change in contact points on the circular contact part 6.

In the configuration above, when the rotary table 2 is rotated, the connector part 7 is driven to bring the movable contacts 7a to 7d into a state being separated from the circular contacts 6a to 6d. Centrifugal force generated by rotating the rotary table 2 is applied to the sample within the biosensor 20. This centrifugal force moves the sample collected in the biosensor 20 into the analytical cavity, as well as centrifugally separates the sample within the analytical cavity.

On the other hand, when the rotary table 2 is brought to a halt, the connector part 7 moves the movable contacts 7a to 7d toward the circular contacts 6a to 6d, and they are brought into the state of contact. With this contact, the electrode of the biosensor 20 and the measuring part 8 are electrically connected via the connector part 7.

As described above, since the electrical relationship between the circular contact part 6 and the connector part 7 is kept unchanged irrespective of the stop position of the rotary table 2 and the rotor 10. Therefore, alignment of the movable contacts of the connector part 7 with the circular contact part 6 becomes unnecessary. In FIG. 1, only one retainer 3 is shown, but it is further possible to provide multiple retainers on one rotary table. In the case above, the retainers are placed at diametrically opposed locations across the rotation center, or a counter balance is provided, in order to achieve a rotating balance of the rotary table.

Figure 2A:
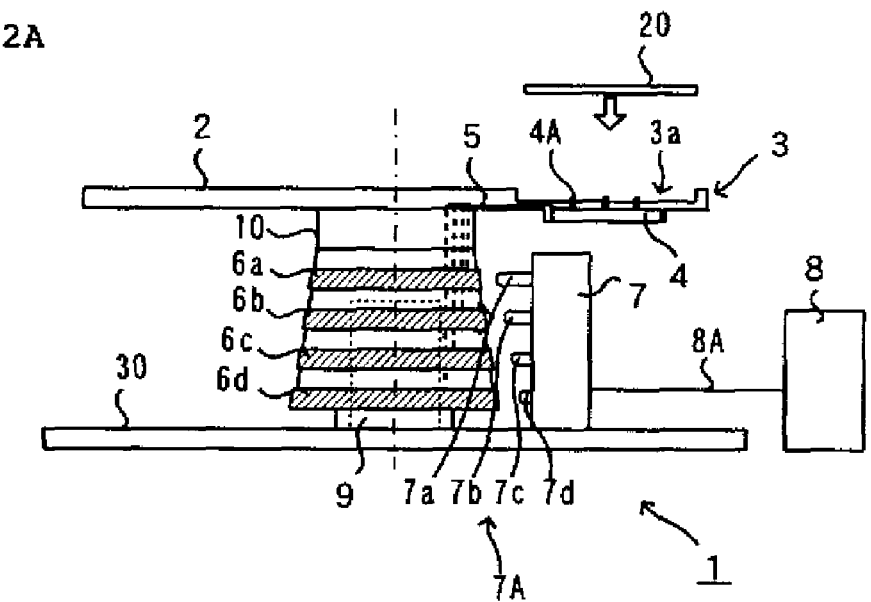
FIG. 2A to FIG. 2C are side views each including a partial sectional view of the centrifugal measuring apparatus according to the first embodiment of the present invention.
Figure 2B:
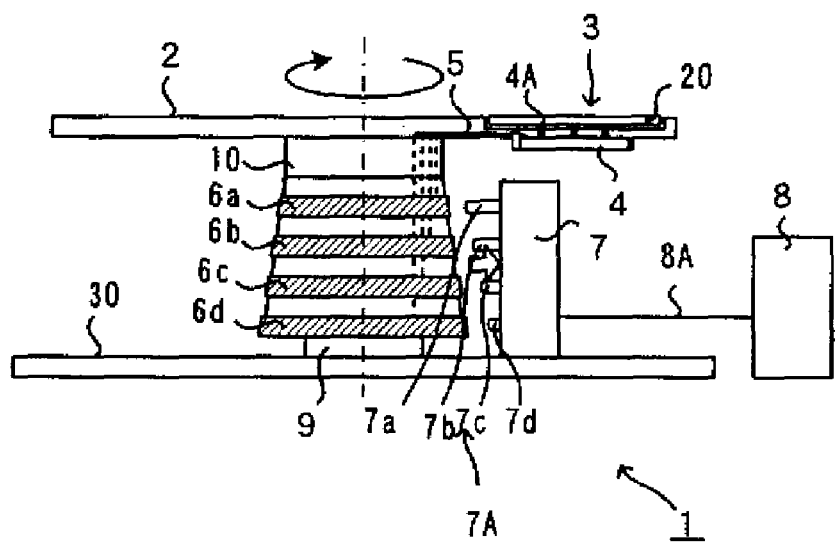
Figure 2C:
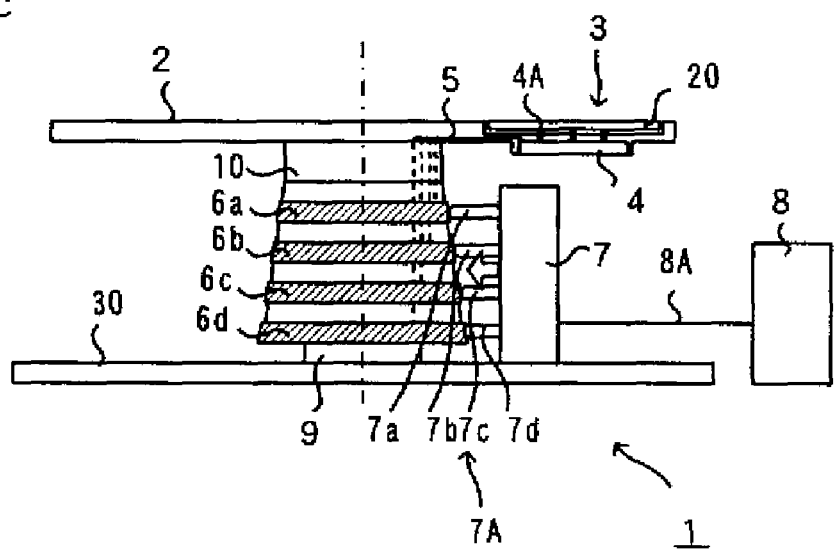
Figure 3A:
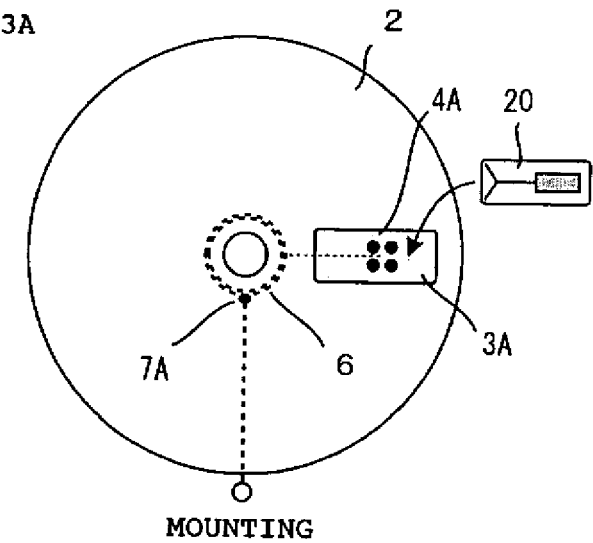
FIG. 3A to FIG. 3D are schematic plan views, viewed from the top of the centrifugal measuring apparatus according to the first embodiment of the present invention.
Figure 3B:
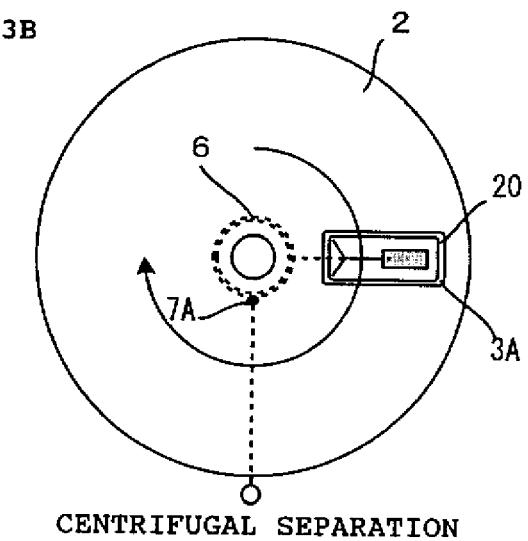
Figure 3C:
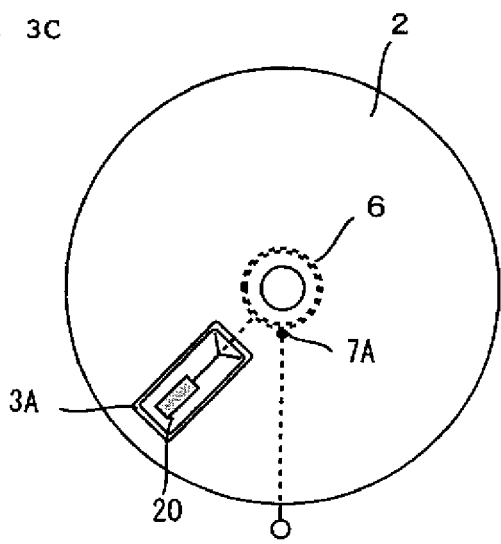
Figure 3D:
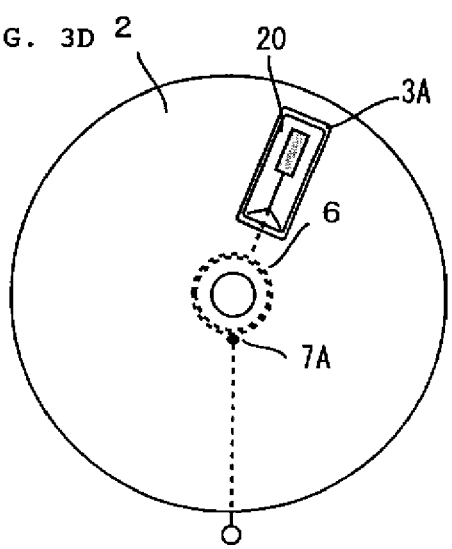

FIG. 2A to FIG. 2C are side views each including a partial sectional view of the centrifugal measuring apparatus according to the first embodiment of the present invention. FIG. 2A illustrates a halt state when the biosensor is mounted and held thereon. FIG. 2B illustrates a rotating state while the biosensor is being held. FIG. 2C illustrates that the rotation is brought to a halt. FIG. 3A to FIG. 3D are schematic plan views, viewed from the top of the centrifugal measuring apparatus according to the first embodiment of the present invention. FIG. 3A illustrates a halt state when the biosensor is mounted and held thereon. FIG. 3B illustrates that the biosensor is held and rotated. FIG. 3C and FIG. 3D illustrate that the rotation is brought to a halt and a measurement is carried out.

In FIG. 2A, the rotary table 2 and the rotor 10 are rotatably supported via the DC motor 9 on the base 30, and the connector part 7 and the measuring part 8 are fixed thereon. Multiple circular contacts 6a to 6d are placed with a predetermined distance therebetween on the outer circumferential surface of the rotor 10 along its axial direction, the rotor being coaxial with the rotary table 2. The movable contacts 7a to 7d of the movable contact part 7A provided on the connector part 7 are placed in such a manner as being opposed respectively to the circular contacts 6a to 6d placed on the rotor 10. A drive mechanism allows the movable contacts 7a to 7d to come into contact with or separate from the circular contacts 6a to 6d.

In FIG. 2A and FIG. 3A, the biosensor 20 is mounted on the retainer and held thereon.

Then, a contact pin (not illustrated in this Figure) of the urged contact part 4 provided on the retainer 3 side is made to abut against the electrode (not illustrated in this Figure) of the biosensor 20, thereby establishing electrical connection. Accordingly, the electrode of the biosensor 20 is electrically connected with the circular contacts 6a to 6d via the urged contact part 4 and the wiring 5.

FIG. 2B and FIG. 3B illustrate that the rotary table 2 and the rotor 10 are rotated while the biosensor 20 is held on the retainer 3. Upon rotating, the connector part 7 moves in the direction to set each movable contacts 7a to 7d of the movable contact part 7A to separate from the circular contacts 6a to 6d, and a high speed rotation is possible in the condition that the rotary table 2 and the rotor 10 are not in contact with the movable contacts 7a to 7d.

With the rotation of the rotary table 2, centrifugal force is applied to the biosensor 20 held in the retainer 3, and the sample in the biosensor 20 is moved and subjected to centrifugal separation.

After the centrifugal separation is finished, rotation of the rotary table 2 is brought to a halt, and a measurement is carried out while holding the biosensor 20 in the retainer 3 of the rotary table 2. FIG. 2C, FIG. 3C, and FIG. 3D each illustrate the state of this measurement. In the state of the measurement, the movable contacts 7a to 7d of the movable contact part 7A of the connector part 7 are moved and made to abut against the circular contacts 6a to 6d, respectively. With the contact between the movable contacts 7a to 7d respectively with the circular contacts 6a to 6d, electrical connection is established between the electrode of the biosensor 20 and the measuring part 8.

As described above, since the circular contacts 6a to 6d are disposed on the circumference of the rotor 10, electrical connection between the movable contacts 7a to 7d and the circular contacts 6a to 6d can be established by moving the movable contacts 7a to 7d, irrespective of the stop position of the rotary table 2 and the rotor 10. FIG. 3C and FIG. 3D illustrate that the rotary table 2 has stopped at different rotational positions. The electrical connection is established by the contact between the movable contacts 7a to 7d and the circular contacts 6a to 6d. Therefore, even when the rotary table 2 stops at a different rotational position, the contact can be established just by moving the movable contacts 7a to 7d towards the circular contacts 6a to 6d, without alignment of the rotational position.

Therefore, while the biosensor 20 is kept on the centrifugal measuring apparatus 1, centrifugal separation and measurement thereafter can be continuously performed.

Figure 4A:
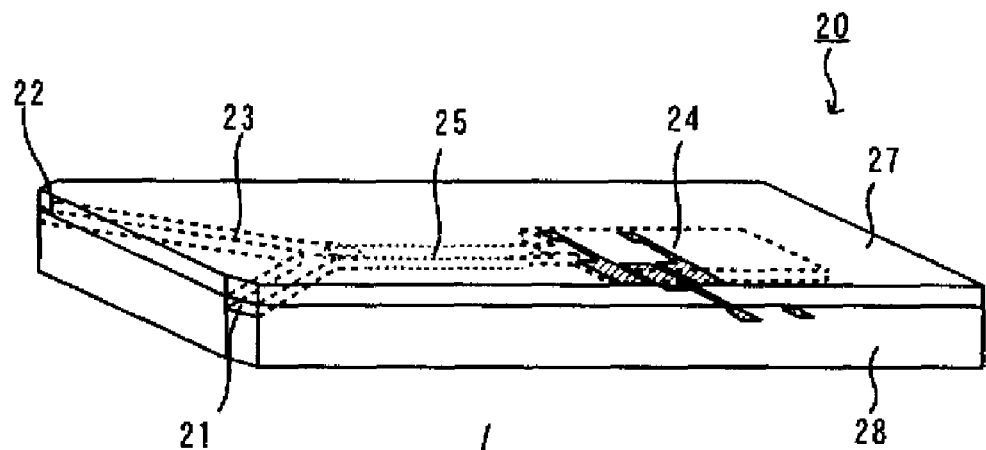
FIG. 4A to FIG. 4C are illustrations to explain a configuration example of a biosensor, a retainer, and an urged contact part, which are used in the centrifugal measuring apparatus according to the present invention.
Figure 4B:
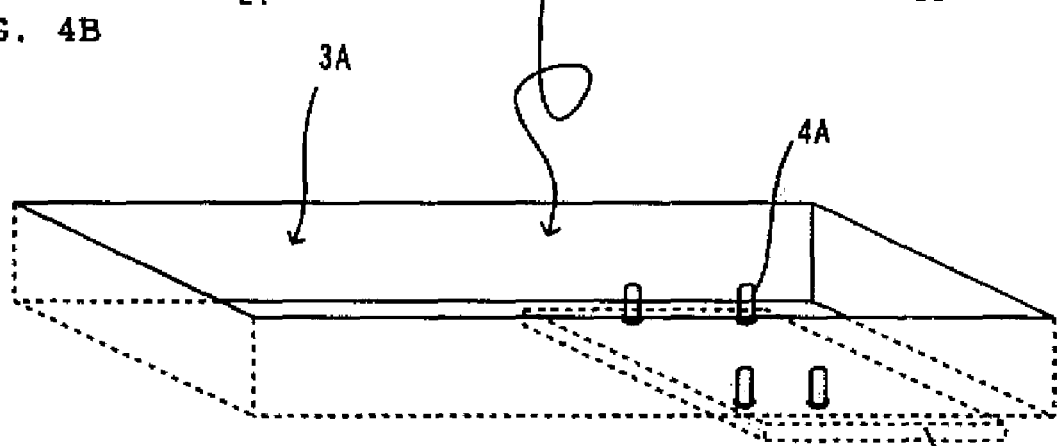
Figure 4C:
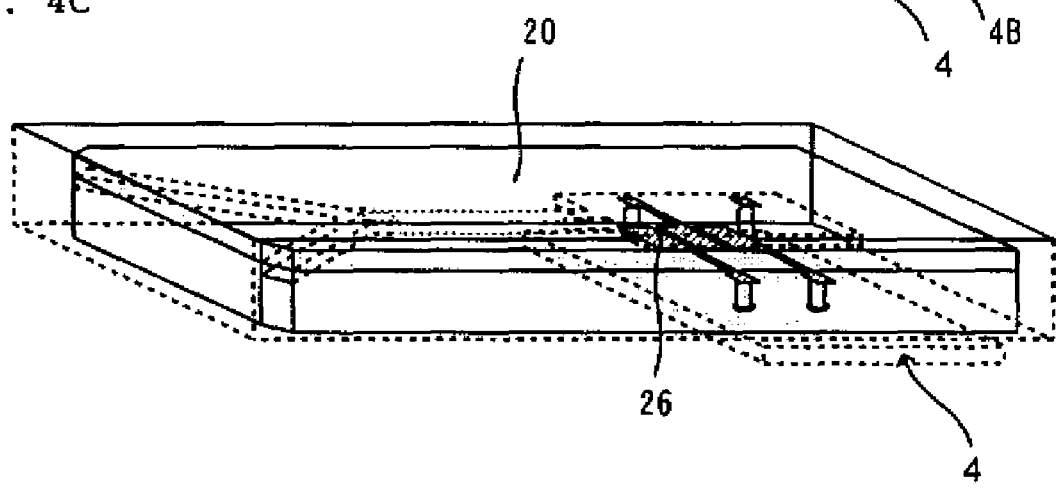

With reference to FIG. 4A to FIG. 4C, there will be explained one configuration example of the biosensor 20, the retainer 3, and the urged contact part 4, which are used for the centrifugal measuring apparatus according to an aspect of the present invention.

The biosensor 20 has a structure obtained by bonding a lower plate 28 and an electrode substrate 27 together. FIG. 4A is a schematic perspective view of the biosensor 20, FIG. 4B is a schematic perspective view of the retainer 3, and FIG. 4C is a schematic perspective view if the biosensor 20 that is held in the retainer 3.

A suction port 21 is provided on one side surface of the biosensor 20, and an air vent 22 is provided on the other side surface. There is provided an opening from the suction port 21 to the air vent 22, the opening being formed by a portion sandwiched between the lower plate 28 and the electrode substrate 27. This opening is a suction cavity 23, which is a space to suck a sample such as a certain amount of blood and to retain the sample temporarily. It is configured such that the blood as a sample is sucked from the suction port 21 by capillary phenomenon, and the air inside the suction cavity 23 is discharged from the air vent 22. After the suction is finished, the suction cavity 23 is filled with the blood. It is to be noted here that either of those openings may be defined as the suction port 21 or the air vent 22 optionally. Therefore, the opening of reference numeral 21 may be defined as the air vent, and the opening of reference numeral 22 may be defined as the suction port.

A suction cavity part connecting to the suction port 21 and a suction cavity part connecting to the air vent 22 are joined inside the biosensor 20, and further connected to a flow channel 25 directing to an analytical cavity 24.

The analytical cavity 24 is provided with a reagent to analyze the blood. When centrifugal force larger than a predetermined level is applied from the outside to the sample such as the blood, the sample is flown into the flow channel 25 from the suction cavity 23, and further introduced into the analytical cavity 24 via the flow channel 25. At this time, a part of the air existing in the analytical cavity 24 passes through the flow channel 25 and the suction cavity 23, to escape to the outside of the analytical cavity 24. The blood flown into the analytical cavity 24 is reacted with the reagent for analysis.

There is a connector window (not illustrated) on the backside of the biosensor 20. Here, it is assumed that the electrode substrate 27 side is defined as a front side, and the lower plate 28 side is defined as a backside, but the front and back sides are defined as such for descriptive purposes. Therefore, the front-back side relationship may be defined the other way around.

In FIG. 4B and FIG. 4C, the urged contact part 4 is placed in the recess of the connector window. The urged contact part 4 includes contact pins 4A (4a to 4d) that are arranged on a substrate 4B. The contact pins 4A are contact terminals that are elastically biased by a spring or the like, and they establish electrical connection with the electrodes 26 placed within the analytical cavity 24 of the biosensor 20. The electrodes 26 are connected with the circular contact 6 via the urged contact part 4, and the electrodes are further electrically connected with the measuring part 8 externally provided, via the connector part 7 as described above, whereby a electrochemical measurement is carried out.

In the configuration above, the electrode substrate 27 constituting the substrate on which the electrodes are disposed, also serves as an upper plate opposed to the lower plate 28.

Figure 5:
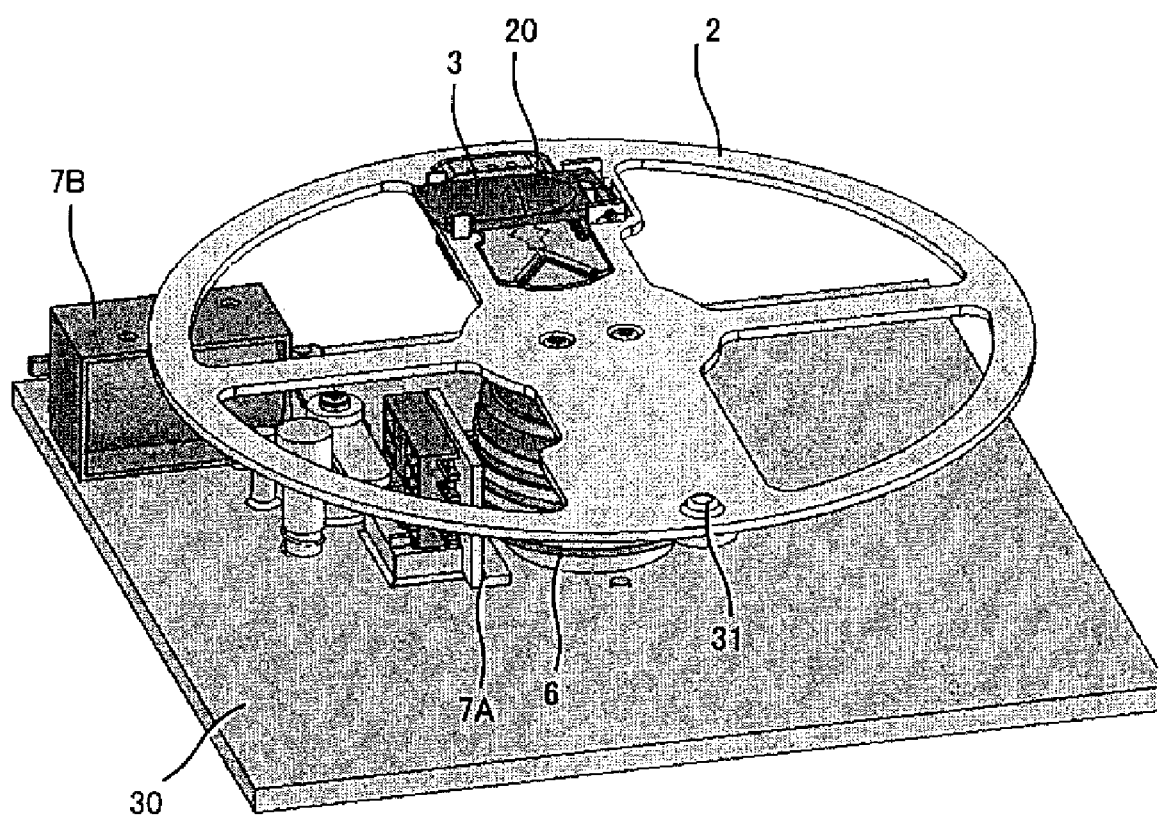
FIG. 5 is an overall view showing a configuration example of the centrifugal measuring apparatus according to the first embodiment of the present invention.
Figure 7:
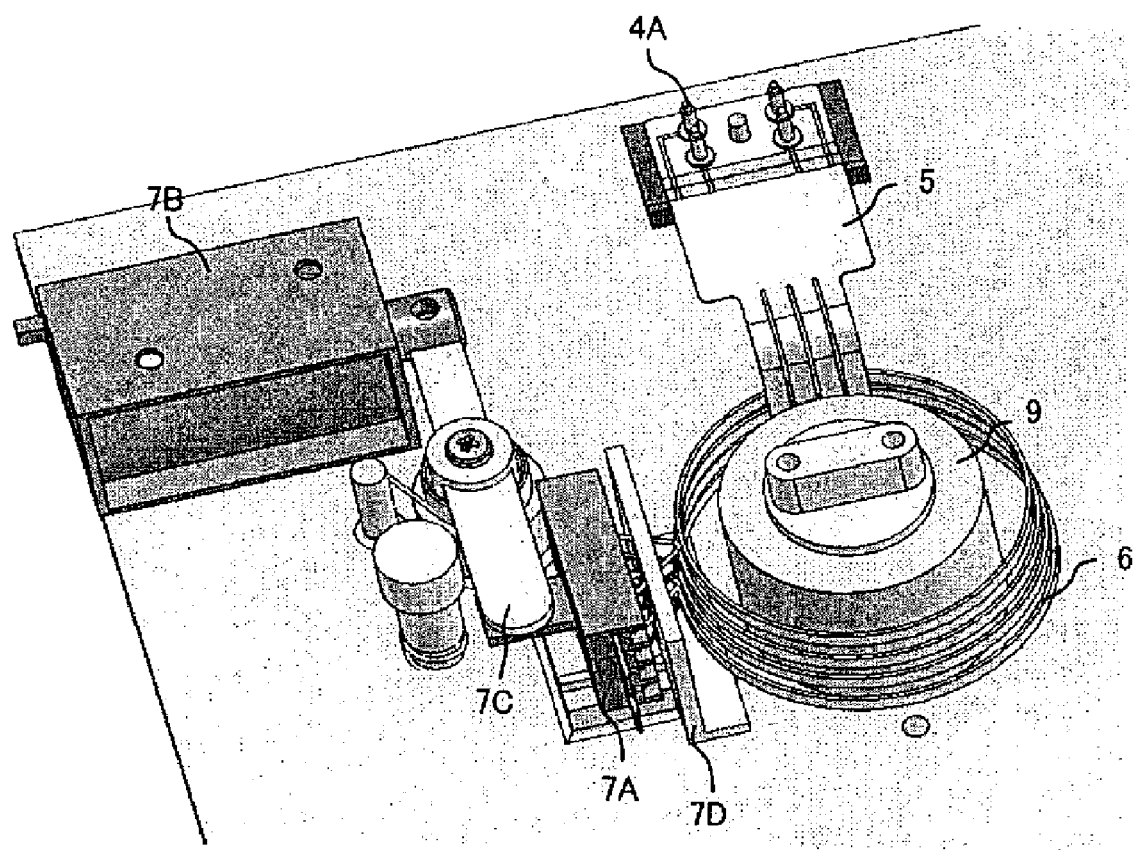
FIG. 7 is an illustration showing a configuration example of the centrifugal measuring apparatus according to the first embodiment of the present invention, in the state where the rotary table is removed therefrom.
Figure 8:
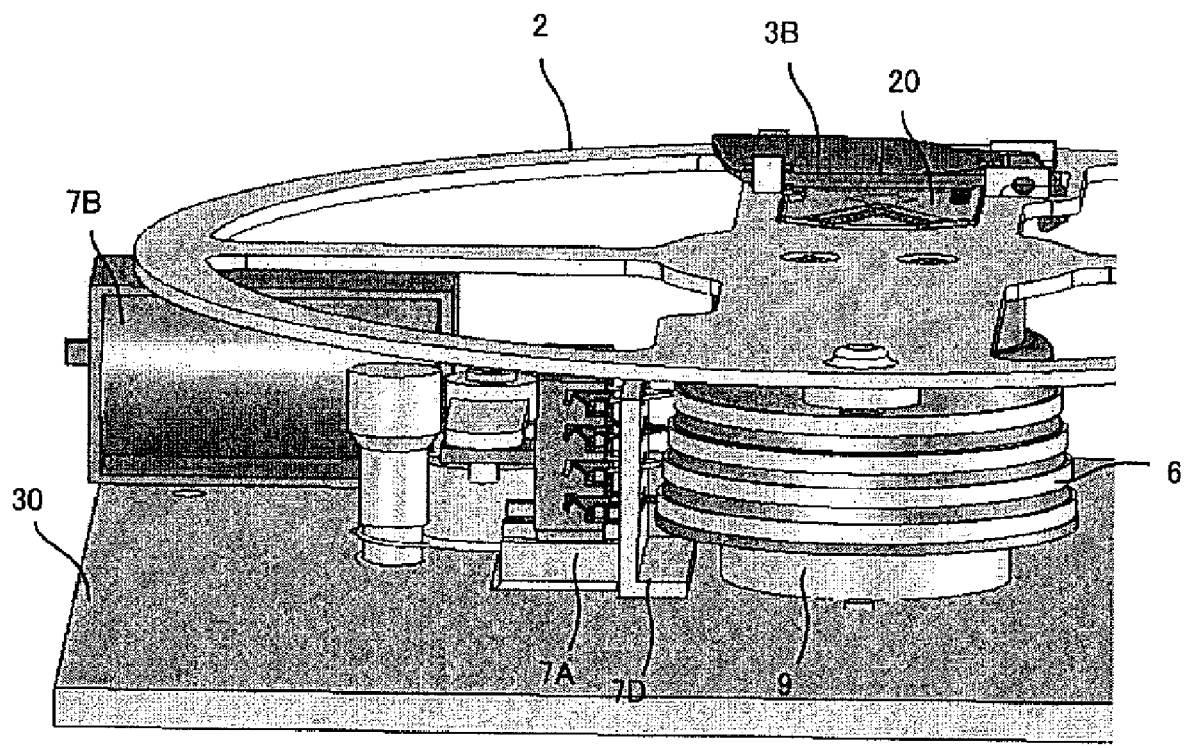
FIG. 8 is a cross sectional view showing a connector part of a configuration example of the centrifugal measuring apparatus according to the first embodiment of the present invention.

A configuration example of the centrifugal measuring apparatus according to the first embodiment of the present invention will be explained with reference to FIG. 5 to FIG. 10. FIG. 5 is an overall view of the centrifugal measuring apparatus, FIG. 6 is a cross sectional view of the centrifugal measuring apparatus, FIG. 7 is an illustration showing a state where the rotary table is removed from the centrifugal measuring apparatus, FIG. 8 is a cross sectional view of the connector part, FIG. 9 is a schematic illustration of the connector part, and FIG. 10 is a cross sectional view of the retainer and the urged contact part.

In FIG. 5, the rotary table 2 and the rotor 10 being coaxial with the rotary table 2 are placed on the base 30, and they are rotationally driven by the motor. The rotary table 2 is provided with the retainer 3 that holds the biosensor 20, and the rotor 10 is provided with the circular contact part 6. The rotary table 2 being illustrated includes a ring shaped part on the outer circumference, and a rib part that links the ring shaped part and the rotation center, and the retainer 3 is formed on the rib part. The counter balance 31 is placed on a position of the rib part diametrically opposed to the retainer 3 across the rotation center.

Furthermore, the connector part 7 is provided on the base 30. The connector part 7 includes movable contact part 7A that electrically connects with the circular contact part 6, and a solenoid 7B and a lever 7C that drive this movable contact part 7A. Movement of the solenoid 7B is transferred to the movable contact part 7A via the lever 7C, so as to operate the movable contact part 7A to come into contact with or to separate from the circular contact part 6.

Figure 6:
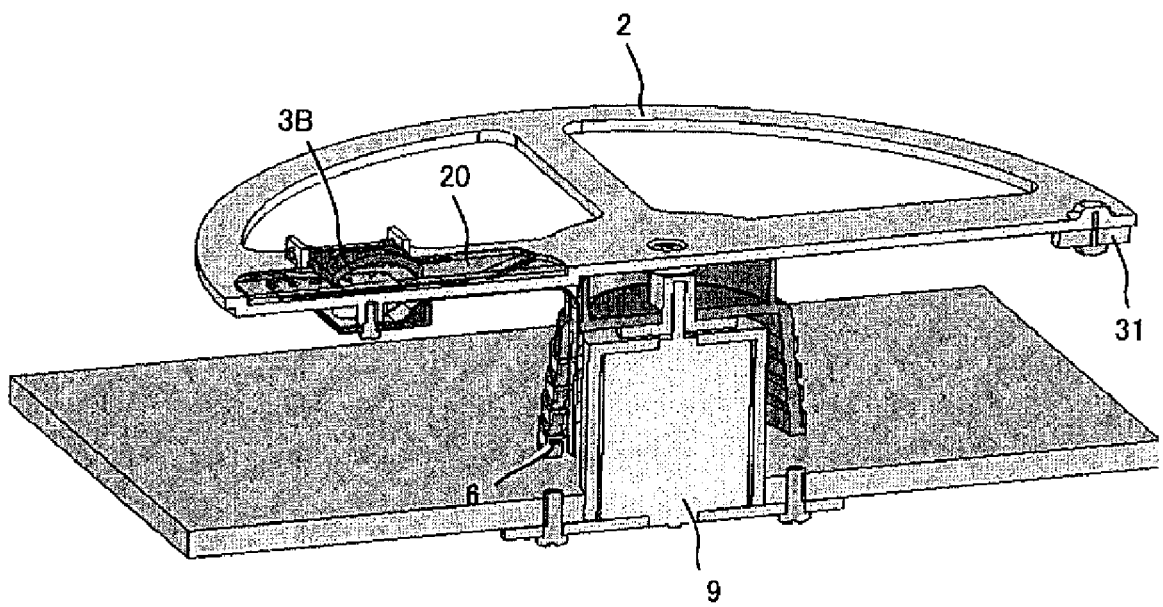
FIG. 6 is a cross sectional view showing a configuration example of the centrifugal measuring apparatus according to the first embodiment of the present invention.

In FIG. 6, the rotor 10 being in a shape of cone or cylinder is provided with the circular contact part 6 on the outer circumferential surface, and it is rotationally driven by the DC motor 9 that is installed inside. The rotary table 2 may be configured as a single piece with the rotary 10, or being joined to the rotary 10, and the rotary table 2 and the rotor 10 are integrally subjected to a rotational drive by the DC motor.

FIG. 7 shows a state where the rotary table and the rotor are removed and the circular contact part and the connector part are exposed. FIG. 8 shows a state where the circular contact part and the connector part are viewed from the side. An electric terminal on one side of the circular contact part 6 is constantly connected to the contact pin 4A of the urged contact part 4 by the wiring 5 such as an FPC. An electric terminal on the other side is selectively connected to the movable contact part 7A of the connector part 7 that is placed at a distance from the circular contact part 6. The DC motor 9 is disposed inside the circular contact part 6.

The connector part 7 is slidably mounted on the bracket 7D that is fixed on the base 30. The bracket 7D determines initial positions of the movable contacts 7a to 7d of the movable contact part 7A provided in the connector part 7 and the circular contacts 6a to 6d. The connector part 7 operates with the solenoid 7B via the lever 7C. When the solenoid 7B moves in a direction, the connector part moves in a direction to be away from the circular contacts 6a to 6d, and when the solenoid 7B moves in the other direction, the connector part moves in a direction approaching the circular contacts 6a to 6d.

As shown in FIG. 9, movable contacts 7a to 7d of the movable contact part 7A are each held elastically with respect to the holder 7E. When the solenoid 7B is driven, the connector part 7 moves in the direction approaching the circular contacts 6a to 6d and comes into contact therewith, whereby electrical connection between the movable contacts 7a to 7d and the circular contacts 6a to 6d is established.

Since the movable contacts 7a to 7d are held elastically with respect to the holder 7E, even when the movable contacts overpass a contact position and have made a move exceedingly towards the circular contacts 6a to 6d more than required, this exceeded move amount is absorbed by this elasticity.

It is to be noted that the movable contacts 7a to 7d as shown in FIG. 9 are each formed in a dogleg shape. However, the shape of the movable contact may be optionally determined, and it is not limited to this dogleg shape.

In FIG. 10, the biosensor 20 stored in a concave portion 3A of the retainer 3 is held by a clip 3B. The contact pin 4A of the urged contact part 4 is placed on the bottom of the concave portion 3A in such a manner as protruding therefrom, and it comes into contact with the electrode of the biosensor 20 that is stored within the concave potion 3A.

Next, with reference to FIG. 11 and FIG. 12A to FIG. 12C, a second configuration example of the centrifugal measuring apparatus according to the first embodiment of the present invention will be explained.

A second example of the first embodiment is a configuration in which the circular contact part 6 is provided on the inner circumferential surface of the rotor 10, and the connector part 7 is placed inside the rotor 10. A member for rotationally driving the rotor 10 is also placed inside the rotor 10 similar to the first configuration example. Alternatively, if there is not enough space for the DC motor 9 due to the existence of the connector part 7, another configuration is possible such as placing the DC motor 9 outside the rotor 10.

The second configuration example may be the same as the first configuration example, except that the circular contact part 6 is placed on the inner circumferential surface of the rotor 10 and the movable contact part 7A of the connector part comes into contact with the circular contact part in the interior of the rotor 10.

Figure 12A:
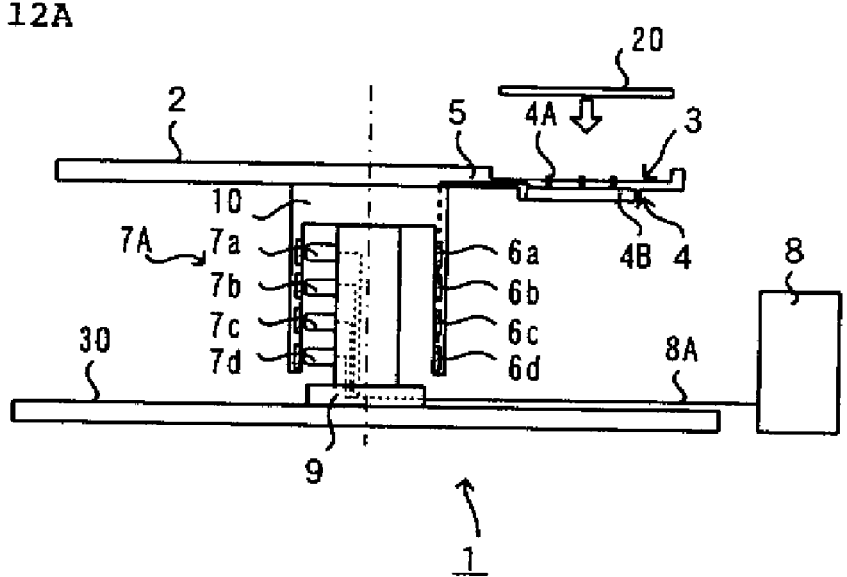
FIG. 12A to FIG. 12C are illustrations to explain the second configuration example of the centrifugal measuring apparatus according to the first embodiment of the present invention.
Figure 12B:
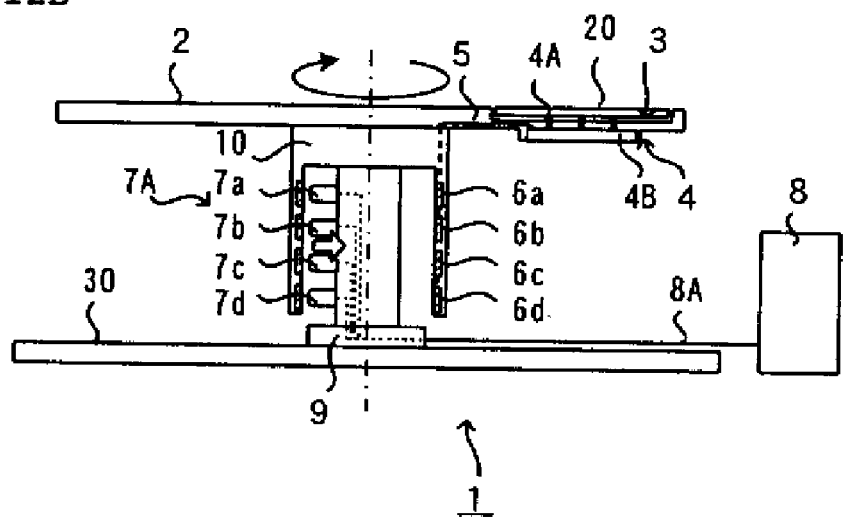
Figure 12C:
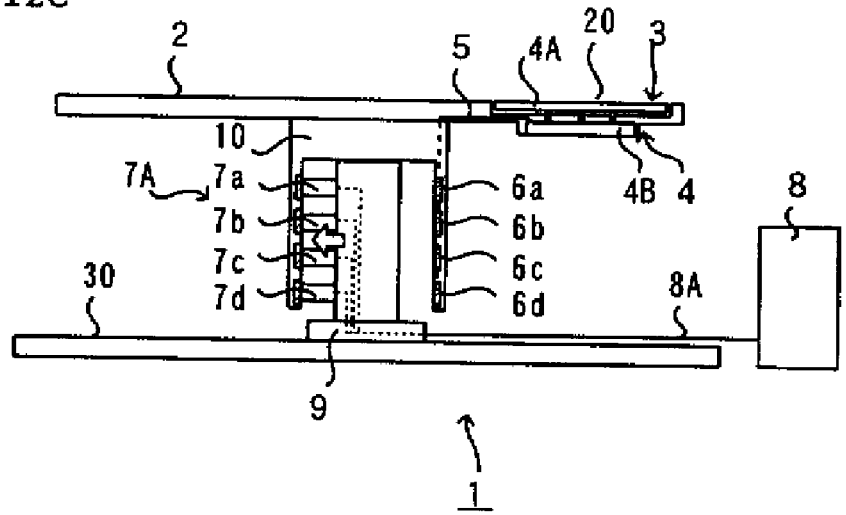

FIG. 12A to FIG. 12C are side views each including a partial cross sectional view of the centrifugal measuring apparatus of the second configuration example. FIG. 12A illustrates a halt state when the biosensor is mounted and held thereon. FIG. 12B illustrates a rotating state while the biosensor is being held. FIG. 12C illustrates that the rotation is brought to a halt.

In FIG. 12A, the rotary table 2 and the rotor 10 are rotatably supported on the base 30 via the DC motor 9. The connector part 7 is placed within the rotor 10 and the measuring part 8 is fixed on the base 30. Multiple circular contacts 6a to 6d are provided with a predetermined distance therebetween along the axial direction on the inner circumferential surface of the rotor 10 that is placed coaxially with the rotary table 2. The movable contacts 7a to 7d of the movable contact part 7A provided in the connector part 7 are arranged in such a manner as respectively opposed to the circular contacts 6a to 6d provided on the rotor 10, and these movable contacts freely come into contact with and separate from the circular contacts 6a to 6d by a drive mechanism. This configuration is different in positional relationship, but it is approximately the same as the configuration example as shown in FIG. 2.

In FIG. 12A, the biosensor 20 is mounted and held on the retainer 3. Then, a contact pin (not illustrated) of the urged contact part 4 placed on the retainer 3 side is made to abut against the electrode (not illustrated) of the biosensor 20, whereby electrical connection is established. Accordingly, the electrode of the biosensor 20 is electrically connected with the circular contacts 6a to 6d via the urged contact part 4 and the wiring 5.

FIG. 12B illustrates that the rotary table 2 and the rotor 10 are rotated while the biosensor 20 is being held on the retainer 3. During the rotation, the connector part 7 is moved in the direction to separate the movable contacts 7a to 7d of the movable contact part 7A from the circular contacts 6a to 6d, and the rotary table 2 and the rotor 10 are allowed to rotate at high speed in the state where the rotary table 2 and the rotor 10 are not in contact with the movable contacts 7a to 7d.

By rotating the rotary table 2, centrifugal force is applied to the biosensor 20 held on the retainer 3, and the sample is moved and subjected to the centrifugal separation in the biosensor 20.

After the centrifugal separation is finished, the rotation of the rotary table 2 is brought to a halt, and a measurement is carried out while the biosensor 20 is kept in the retainer 3 of the rotary table 2. FIG. 12C illustrates a state where the measurement is carried out. In the state of the measurement, the movable contacts 7a to 7d of the movable contact part 7A of the connector part 7 are moved and made to abut against the circular contacts 6a to 6d, respectively. With the contact between the movable contacts 7a to 7d respectively with the circular contacts 6a to 6d, electrical connection is established between the electrode of the biosensor 20 and the measuring part 8.

As described above, since the circular contacts 6a to 6d are disposed on the circumference of the rotor 10, electrical connection between the movable contacts 7a to 7d and the circular contacts 6a to 6d can be established by moving the movable contacts 7a to 7d, irrespective of the stop position of the rotary table 2 and the rotor 10. The electrical connection is established when the movable contacts 7a to 7d come into contact with the circular contacts 6a to 6d. Therefore, even when the rotary table 2 stops at a different rotational position, the connection can be established just by moving the movable contacts 7a to 7d towards the circular contacts 6a to 6d to come into contact therewith, without alignment of the rotational position.

Therefore, in the state where the biosensor 20 is kept on the centrifugal measuring apparatus 1, centrifugal separation and a measurement thereafter can be continuously performed.

Next, with reference to FIG. 13 to FIG. 15C, a third configuration example of the centrifugal measuring apparatus according to the first embodiment of the present invention will be explained.

The third example of the first embodiment has a configuration in which the circular contact part 6 is provided on a board face of the rotary table 2, and the connector part 7 is provided on a fixed portion that is opposed to the rotary table 2 in the axial direction. A member for rotationally driving the rotor 10 may be placed inside the rotor 10 similar to the first configuration example. Alternatively, similar to the second example, another configuration is possible such as placing the driving member outside the rotor 10.

The third configuration example may be approximately the same as the first and second configuration example, except that the circular contact part 6 is placed on the board face of the rotary table 2, this circular contact part 6 is electrically connected to the urged contact part 4 via the wiring 5, and the movable contact part 7A of the connector part 7 is provided on the side opposed, in the direction of rotary shaft, to the circular contact part 6 placed on the rotary table 2, to come into contact with the circular contact part 6.

Figure 13:
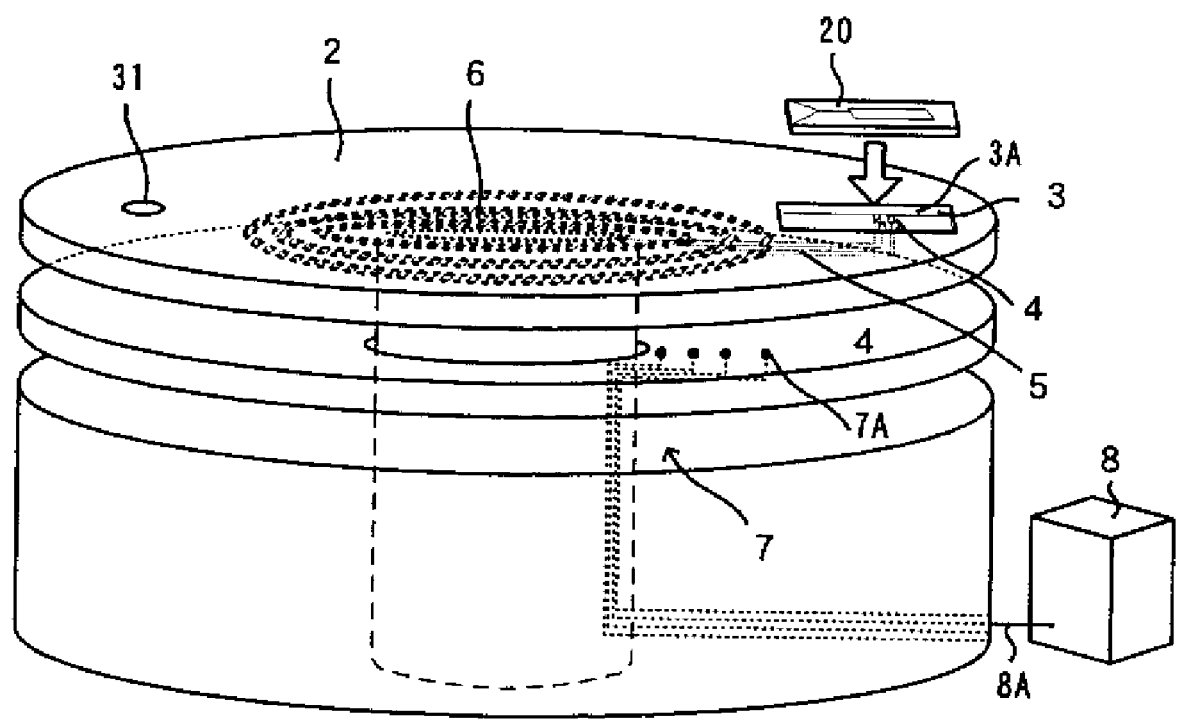
FIG. 13 is a schematic illustration to explain a third configuration example of the centrifugal measuring apparatus according to the first embodiment of the present invention.

FIG. 13 is an illustration to explain the third configuration example of the centrifugal measuring apparatus according to the first embodiment of the present invention. Hereinafter, only a configuration different from the first and second examples will be explained, and tedious explanation will not be made for the parts in common.

The centrifugal measuring apparatus 1 is provided with a rotary table 2 being rotationally driven, a retainer 3 that holds a biosensor 20 on the rotary table 2, an urged contact part 4 that abuts against an electrode (not illustrated in this Figure) provided in the biosensor 20 to establish electrical connection, a measuring part 8 that measures a signal from the electrode in the biosensor 20, and a connector part 7 that selectively establishes electrical connection between the urged contact part 4 and the measuring part 8.

A circular contact part 6 is arranged on the rotary table 2, including circular contacts concentrically provided, in such a manner as being coaxial with the center of the rotation. Each of the circular contacts is electrically connected to the urged contact part 4 and the wiring 5. The urged contact part 4 brings a contact pin into contact with the electrode, and electric connection with the electrode of the biosensor 20 held by the retainer 3 is established. The circular contact part 6 includes multiple circular contacts 6a to 6d concentrically placed on the board face of the rotary table 2 radially with a predetermined distance therebetween. The number of the circular contacts 6a to 6d may be equal to the number of the electrode of the biosensor 20 and also equal to the number of the point of contact in the urged contact part 4, thereby establishing electrical connection with each point of contact in the urged contact part 4. The circular contact part 6 is electrically connected with the urged contact part 4 by the wiring 5 such as flexible wiring or printed wiring placed on the rotary table 2.

In the meantime, the connector part 7 is placed on the side being opposed to the rotary table 2 in the axial direction, and movable contact part 7A is provided on the connector part 7 in such a manner as opposed to the circular contacts 6a to 6d. The movable contact part 7A is allowed to freely come into contact to or separate from the circular contact part 6, and provided with movable contacts 7a to 7d that are accessible to the circular contacts 6a to 6d, respectively. For example, a mechanism to make the movable contacts 7a to 7d to be movable may be configured by providing a lifting and lowering device that moves up and down a member on which the movable contacts 7a to 7d are provided.

For instance, this lifting and lowering device may be a transfer mechanism (not illustrated in this Figure) utilizing a solenoid.

By driving this transfer mechanism, the movable contacts 7a to 7d are allowed to abut against the circular contacts 6a to 6d for establishing electrical connection, or to separate therefrom for shutting off the electrical connection.

The connector part 7 is connected to the measuring part 8. The electrode in the biosensor 20 is energized via the connector part 7, from the measuring part 8 or a power source not illustrated, and on the other hand, a measured signal from the electrode of the biosensor 20 is transferred to the measuring part 8 via the connector part 7.

The rotary table 2 is turned by a motor (not illustrated in this Figure) whereas the connector part 7 and the measuring part 8 are fixed. It is to be noted here, as a way of example, the connector part 7 and the measuring part 8 may be connected via wiring 8A.

The circular contact part 6 and the urged contact part 4 are electrically connected via the wiring 5 provided on the rotary table 2. Therefore, even in the case where the rotary table 2 is rotated and a rotational position is changed, electrical relationship among the circular contact part 6, the urged contact part 4, and the connector part 7 are unchanged, since their positional relationship is changed only about a contact point on the circular contact part 6.

In the configuration above, when the rotary table 2 is rotated, the connector part 7 is moved down, and some distance is put between the movable contacts 7a to 7d and the circular contacts 6a to 6d. Centrifugal force generated by rotating the rotary table 2 is applied to the sample within the biosensor 20. This centrifugal force moves the sample collected in the biosensor 20 into the analytical cavity, as well as centrifugally separates the sample within the analytical cavity.

On the other hand, when the rotary table 2 is brought to a halt, the connector part 7 is raised, and the movable contacts 7a to 7d are moved towards the circular contacts 6a to 6d to come into contact therewith. With this contact, the electrode of the biosensor 20 and the measuring part 8 are electrically connected via the connector part 7.

As described above, the electrical relationship between the circular contact part 6 and the connector part 7 is kept unchanged irrespective of the stop position of the rotary table 2. Therefore, alignment of the movable contacts of the connector part 7 with the circular contact part 6 becomes unnecessary. Though only one retainer 3 is shown in FIG. 13, another configuration may be possible, such as providing multiple retainers on one rotary table. Also in the case above, the retainers are placed at diametrically opposed locations via the rotation center, or a counter balance is provided, in order to achieve a rotating balance of the rotary table.

Figure 14A:
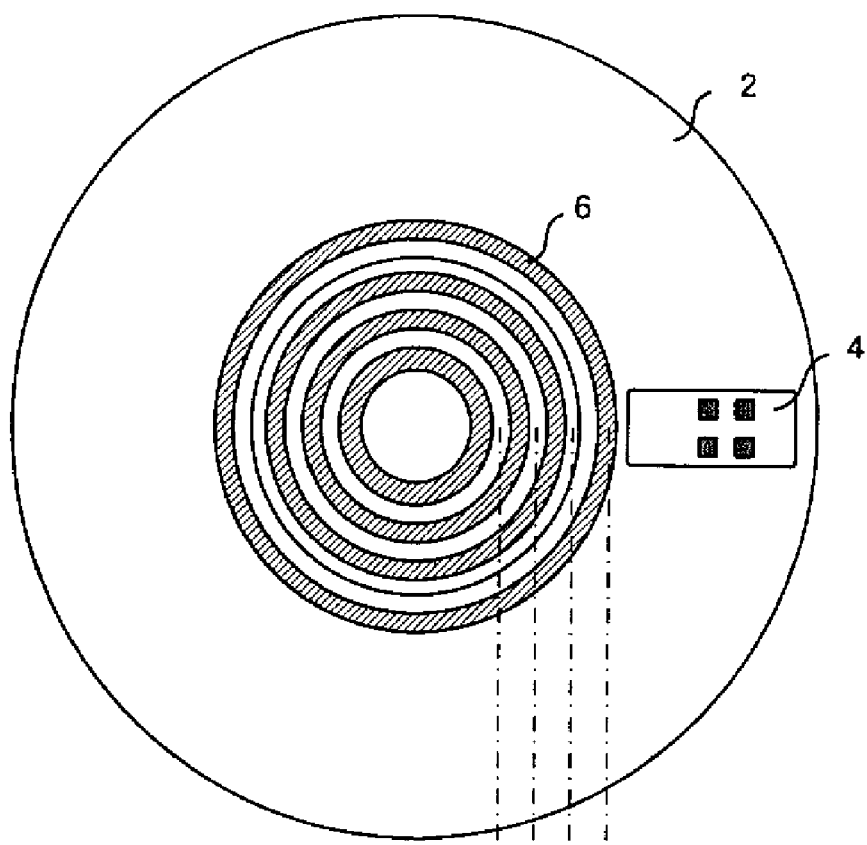
FIG. 14A and FIG. 14B are schematic illustrations to explain the third configuration example of the centrifugal measuring apparatus according to the first embodiment of the present invention.

FIG. 14A shows one face of the rotary table 2. On this face of the rotary table 2, the urged contact part 4 and the circular contact part 6 are placed. In the example as shown in FIG. 14A, the circular contact part 6 is placed concentrically at radially inner side of the urged contact part 4. However, the circular contact part 6 may be placed at a location overlapping the urged contact part 4 or in the outer side thereof, by configuring the urged contact part 4 to be built in the rotary table 2.

Figure 14B:
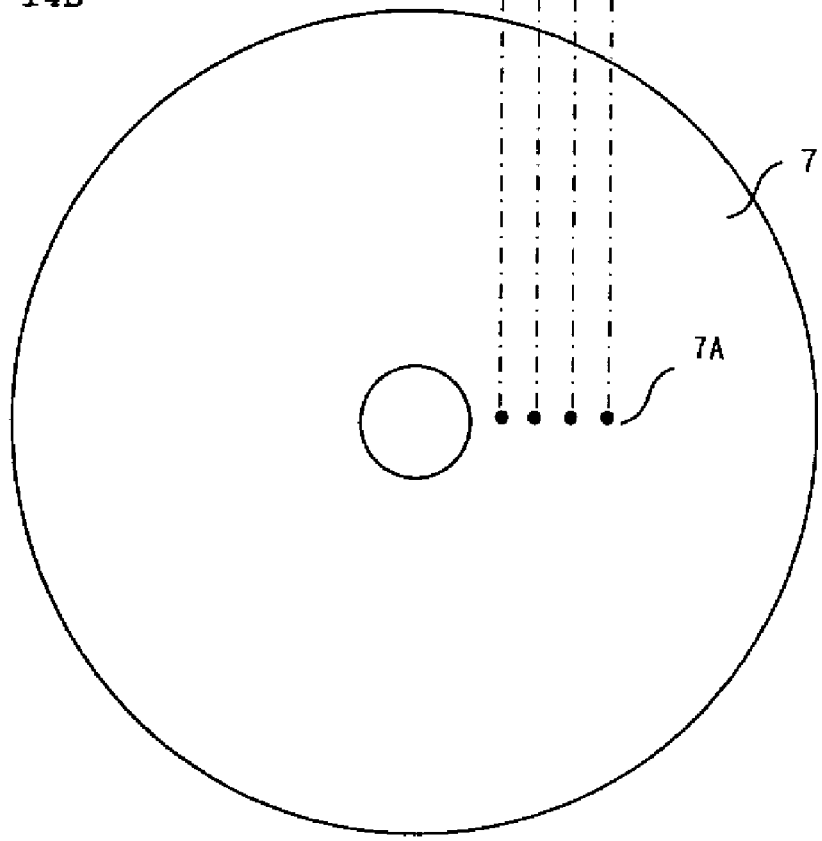

FIG. 14B shows a configuration of the movable contact part 7A on the connector part 7. This movable contact part 7A is placed on the plane facing to the circular contact part 6 of the rotary table 2, in such a manner as opposed to the circular contact part 6. In FIG. 14B, the points of contact of the movable contact part 7A are arranged in a line. However, these points of contact of the movable contact part 7A may be positioned at any locations as far as the locations are opposed to the circular contacts 6a to 6d, respectively, and arrangement in a line is not necessarily required.

Figure 15A:
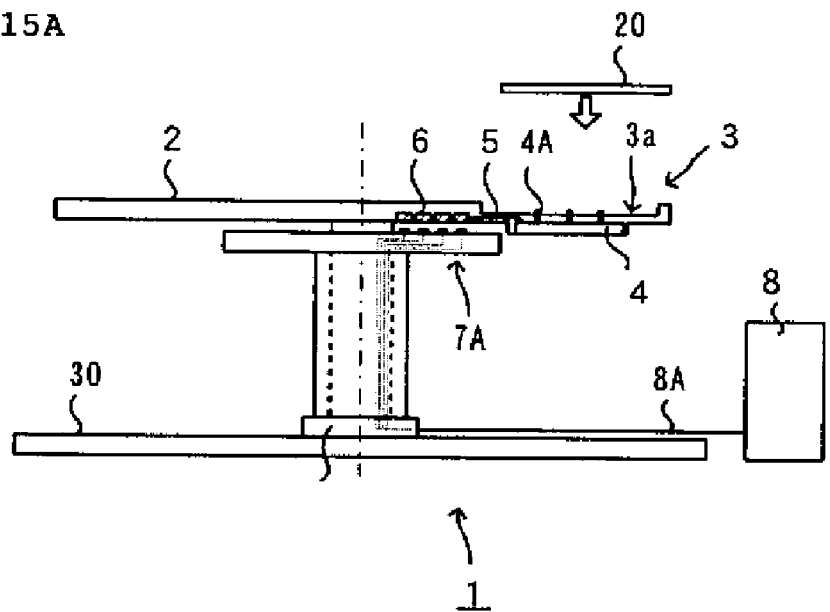
FIG. 15A to FIG. 15C are side views each including a partial sectional view of the third configuration example of the centrifugal measuring apparatus according to the first embodiment of the present invention.
Figure 15B:
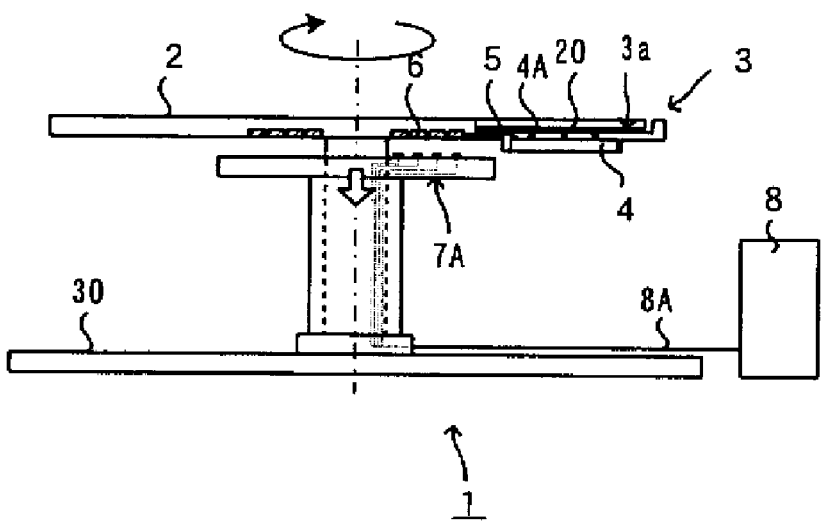
Figure 15C:
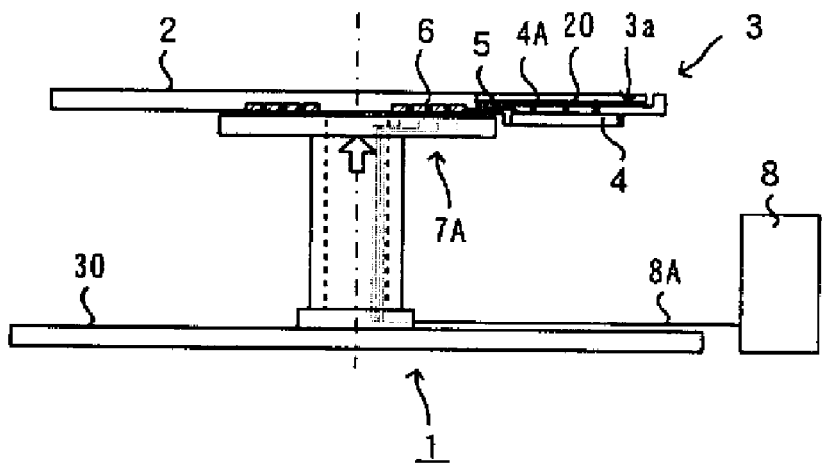

FIG. 15A to FIG. 15C are side views each including a partial sectional view of the centrifugal measuring apparatus according to the third configuration example of the present invention. FIG. 15A illustrates a halt state when the biosensor is mounted and held thereon. FIG. 15B illustrates a rotating state while the biosensor is being held. FIG. 15C illustrates that the rotation is brought to a halt.

In FIG. 15A, on the base 30, the rotary table 2 is placed that is rotationally driven by the DC motor 9. The connector part 7 and the measuring part 8 are fixed on the base 30.

On the board face of the rotary table 2, the face being opposed to the connector part 7, multiple circular contacts 6a to 6d are provided with a predetermined distance therebetween, coaxially with the rotary table 2 about the rotary shaft.

The movable contacts 7a to 7d of the connector part 7 are arranged in such a manner as opposed to the circular contacts 6a to 6d provided on the rotary table 2, and these movable contacts freely come into contact with and separate from the circular contacts 6a to 6d by a lifting and lowering mechanism (not illustrated in this Figure). In FIG. 15A, the biosensor 20 is mounted on the retainer 3 and held thereon. Then, a contact pin (not illustrated in this Figure) of the urged contact part 4 placed on the retainer 3 is made to abut against the electrode (not illustrated in this Figure) of the biosensor 20, thereby establishing electrical connection. Accordingly, the electrode of the biosensor 20 is electrically connected to the circular contacts 6a to 6d via the urged contact part 4 and the wiring 5.

FIG. 15B illustrates a state in which the rotary table 2 is rotated with the biosensor 20 being held on the retainer 3. During the rotation, the connector part 7 moved in the direction (lower direction in the figure) to separate the movable contacts 7a to 7d of the movable contact part 7A respectively from the circular contacts 6a to 6d, and the rotary table 2 is allowed to rotate at high speed in the state where the rotary table 2 is not in contact with the movable contacts 7a to 7d.

By rotating the rotary table 2, centrifugal force is applied to the biosensor 20 held on the retainer 3, and the sample is moved and subjected to the centrifugal separation in the biosensor 20.

After the centrifugal separation is finished, the rotation of the rotary table 2 is brought to a halt, and a measurement is carried out while the biosensor 20 is kept in the retainer 3 of the rotary table 2. FIG. 15C illustrates a state where the measurement is carried out. In the state of the measurement, the movable contacts 7a to 7d of the movable contact part 7A of the connector part 7 are moved and made to abut against the circular contacts 6a to 6d, respectively. With the contact between the movable contacts 7a to 7d respectively with the circular contacts 6a to 6d, electrical connection is established between the electrode of the biosensor 20 and the measuring part 8.

As described above, since the circular contacts 6a to 6d are disposed at the board face of the rotary table 2, electrical connection between the movable contacts 7a to 7d and the circular contacts 6a to 6d can be established by moving the movable contacts 7a to 7d, irrespective of the stop position of the rotary table 2. The electrical connection is established when the movable contacts 7a to 7d come into contact with the circular contacts 6a to 6d. Therefore, even when the rotary table 2 stops at a different rotational position, the connection can be established just by moving the movable contacts 7a to 7d towards the circular contacts 6a to 6d to come into contact therewith, without alignment of the rotational position. Therefore, in the state where the biosensor 20 is kept on the centrifugal measuring apparatus 1, centrifugal separation and a measurement thereafter can be continuously performed.

In the first and second configurations as described above, the length of the rotor becomes longer, as the circular contacts grow in number. On the other hand, according to the third configuration, the length of the rotor can be kept unchanged since the circular contacts are placed on the board face of the rotary table 2.

Next, with reference to FIG. 16 and FIG. 17, a centrifugal measuring apparatus according to a second embodiment of the present invention will be explained. In the second embodiment, the circular contacts are provided on the fixed member side, whereas the first embodiment as described above is directed to a configuration in which the circular contacts are placed on a rotating member such as the rotary table and the rotor.

Figure 16:
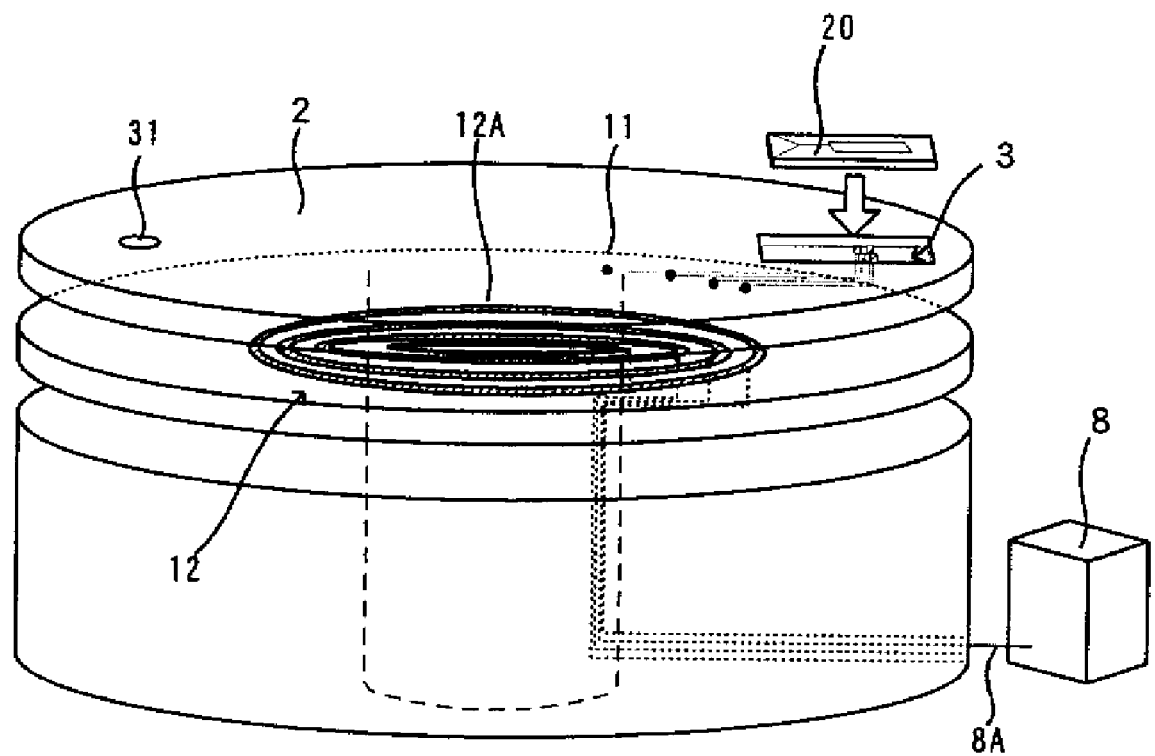
FIG. 16 is a schematic illustration to explain a configuration example of a centrifugal measuring apparatus according to a second embodiment of the present invention.

FIG. 16 is a schematic illustration to explain a configuration example of the centrifugal measuring apparatus according to the second embodiment of the present invention. The second embodiment includes the circular contact part and the movable contact part having a relationship being reverse of the relationship of the third configuration example of the first embodiment as shown in FIG. 13.

Similar to the first embodiment, the centrifugal measuring apparatus according to the second embodiment of the present invention is provided with a rotary table 2 being rotationally driven by a motor, a retainer 3 that holds a biosensor 20 on the rotary table 2, an urged contact part 4 that abuts against the electrode (not illustrated in this Figure) provided in the biosensor 20 to establish electrical connection, a measuring part 8 that measures a signal from the electrode in the biosensor 20, and a connector part 12 that selectively establishes electrical connection between the urged contact part 4 and the measuring part 8.

In the second embodiment, there are provided a point of contacts 11 that is electrically connected to the urged contact part 4, on a circle along the circumference of the rotary shaft of the rotary table 2. The connector part 12 is provided with the circular movable contact 12A that freely come into contact with and separate from the point of contact 11 on the rotary table 2, at any circular position.

Figure 17A:
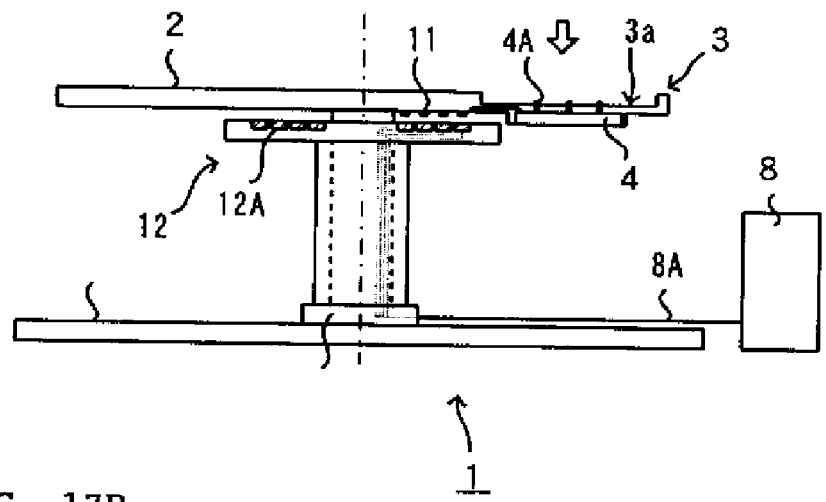
FIG. 17A to FIG. 17C are side views each including a partial sectional view of the centrifugal measuring apparatus according to the second embodiment of the present invention.
Figure 17B:
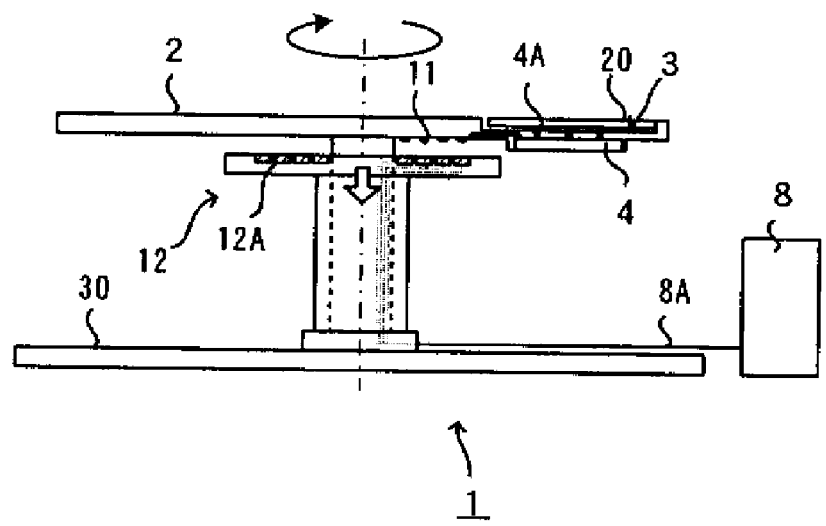
Figure 17C:
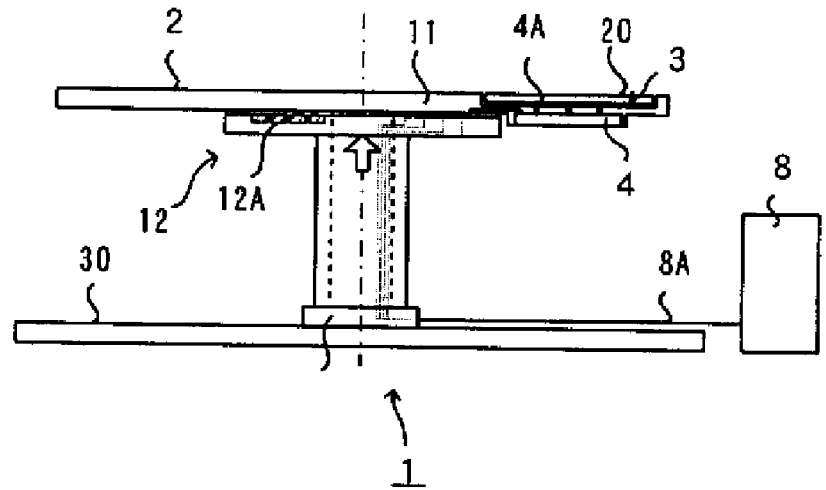

FIG. 17A to FIG. 17C are side views each including a partial cross sectional view of the centrifugal measuring apparatus according to the second embodiment. FIG. 17A illustrates a halt state when the biosensor is mounted and held thereon. FIG. 17B illustrates a rotating state while the biosensor is being held. FIG. 17C illustrates that the rotation is brought to a halt.

In FIG. 17A, the rotary table 2 being rotationally driven is placed on the base 30. The connector part 12 and the measuring part 8 are fixed on the base 30.

Multiple circular movable contacts 12A are arranged on the side opposed to the points of contact 11 on the rotary table 2, with a predetermined distance therebetween concentrically about the rotary shaft, and these circular movable contacts freely come into contact with and separate from the points of contact 11 by a lifting and lowering mechanism (not illustrated).

In FIG. 17A, the biosensor 20 is mounted on the retainer 3 and held thereon.

Then, a contact pin (not illustrated in this Figure) of the urged contact part 4 placed on the retainer 3 is made to abut against the electrode (not illustrated in this Figure) of the biosensor 20, thereby establishing electrical connection.

Accordingly, the electrode of the biosensor 20 is electrically connected to the point of contact 11 via the urged contact part 4 and the wiring 5.

FIG. 17B illustrates a state in which the rotary table 2 is rotated while the biosensor 20 is being held on the retainer 3. During the rotation, the connector part 7 is moved in the direction (lower direction in the figure) to separate the circular movable contact 12A from the point of contact 11 on the rotary table 2 side, and the rotary table 2 is allowed to rotate at high speed in the state where the rotary table 2 is not in contact with the circular movable contact 12A.

By rotating the rotary table 2, centrifugal force is applied to the biosensor 20 held on the retainer 3, and the sample is moved and subjected to the centrifugal separation in the biosensor 20.

After the centrifugal separation is finished, rotation of the rotary table 2 is brought to a halt, and a measurement is carried out while holding the biosensor 20 in the retainer 3 of the rotary table 2. FIG. 17C illustrates the state of this measurement. In the state of the measurement, the circular movable contact 12A of the contact part 12 is moved and made to abut against the point of contact 11. With the contact between the circular movable contact 12A with the point of contact 11, electrical connection is established between the electrode of the biosensor 20 and the measuring part 8.

As described above, since the point of contact 11 is disposed at the board face of the rotary table 2, electrical connection between the circular movable contact 12A and the point of contact 11 can be established by moving the circular movable contact 12A, irrespective of the stop position of the rotary table 2. The electrical connection is established by the contact between the circular movable contact 12A and the point of contact 11. Therefore, even when the rotary table 2 stops at a different rotational position, the contact can be established just by moving the circular movable contact 12A towards the point of contact 11, to establish contact therebetween, without alignment of the rotational position. Therefore, in the state where the biosensor 20 is kept on the centrifugal measuring apparatus 1, centrifugal separation and a measurement thereafter can be continuously performed.

According to the second embodiment, similar to the third configuration of the first embodiment, the length of the rotor can be kept unchanged since the point of contact is placed on the board face of the rotary table 2.

Figure 18A:
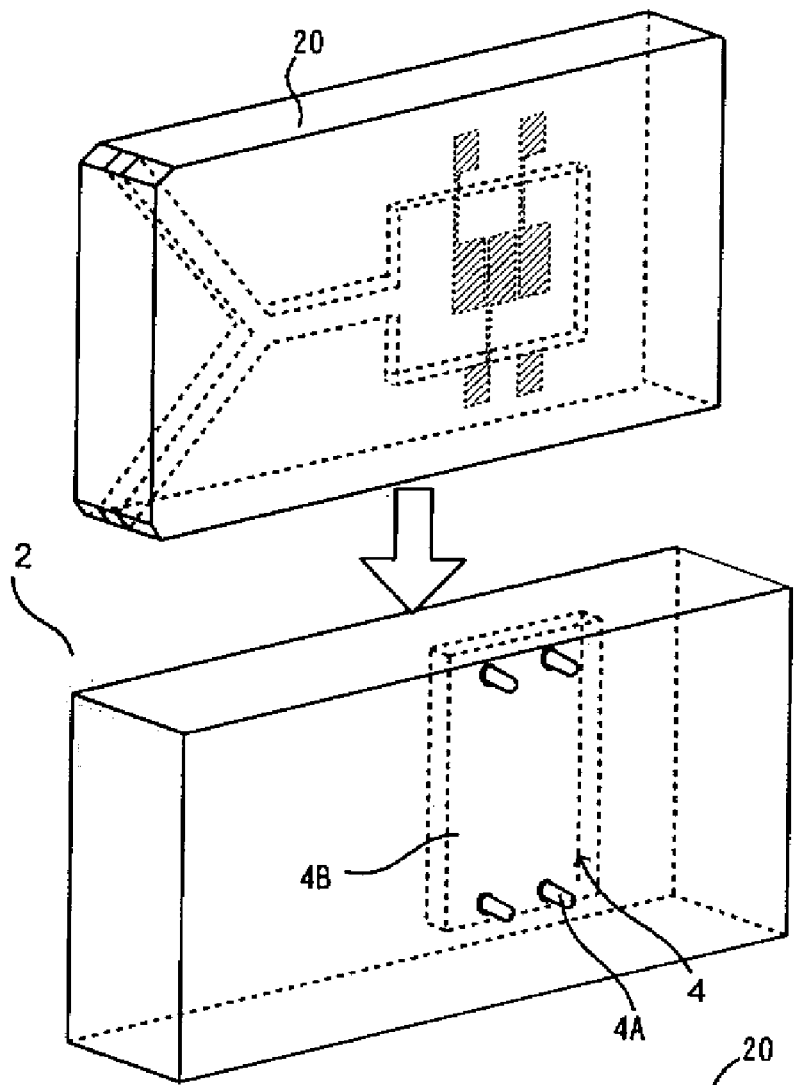
FIG. 18A and FIG. 18B are illustrations to explain how the biosensor is mounted on the rotary table of the centrifugal measuring apparatus according to the present invention.
Figure 18B:
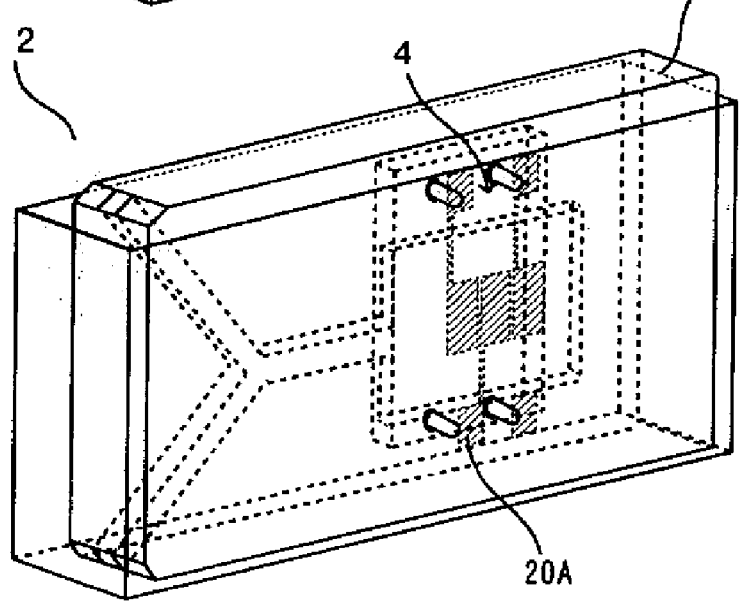

In each of the configuration example as described above, the biosensor 20 is arranged so that a planar part of the biosensor 20 is set to be almost horizontal with the rotary table 2. However, it is also possible to mount the biosensor 20 to be set with a predetermined tilt angle with respect to the rotary table 2. Alternatively, the planar part of the biosensor 20 may be set to be almost vertical with the rotary table 2. FIG. 18A and FIG. 18B are illustrations to explain the state how the biosensor 20 is mounted on the rotary table.

The rotary table 2 is provided with a concave part 3A to store the biosensor 20 in such a manner that planar part of the biosensor is set to be almost in an upright position. The urged contact part 4 is provided on the side surface of the concave part 3A, and the contact pin 4A being elastically urged by a spring or the like protrudes a little towards the inner side of the concave part 3A.

FIG. 18B illustrates a state in which the biosensor 20 is stored within the concave part 3A. The electrode 20A of the biosensor 20 is stored within the concave part 3A and comes into contact with the contact pin 4A, thereby establishing electrical connection. With the arrangement as described above, a large number of biosensors 20 can be placed on the rotary table 2.

Figure 19A:
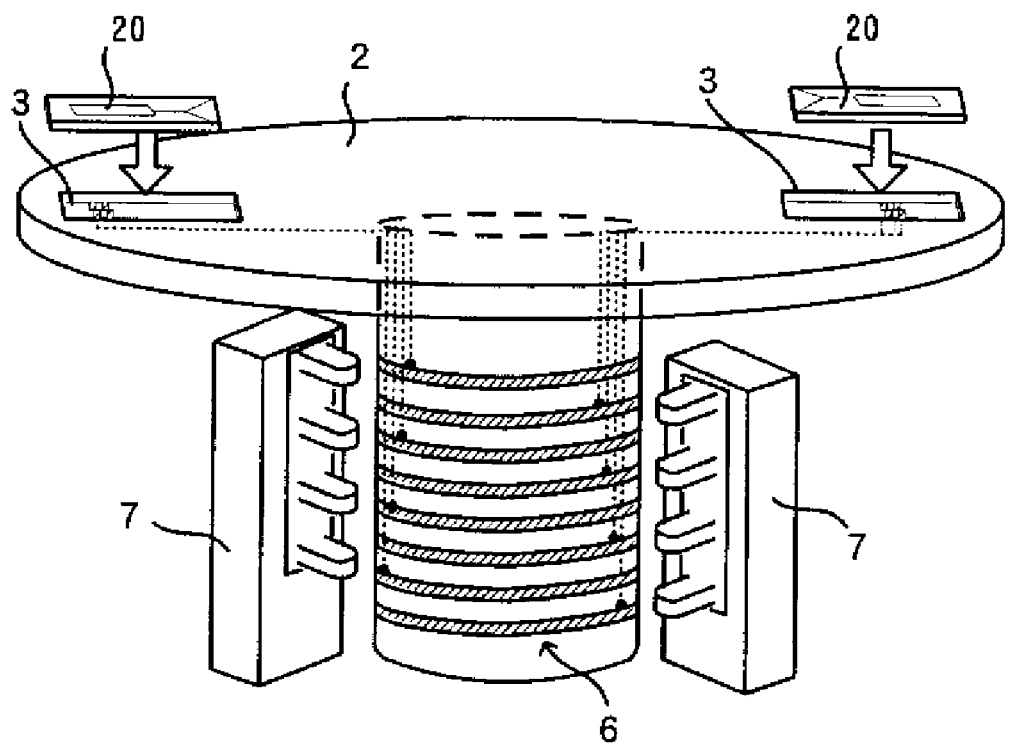
FIG. 19A and FIG. 19B are illustrations to explain the configuration to arrange multiple biosensors on the rotary table of the centrifugal measuring apparatus according to the present invention.
Figure 19B:
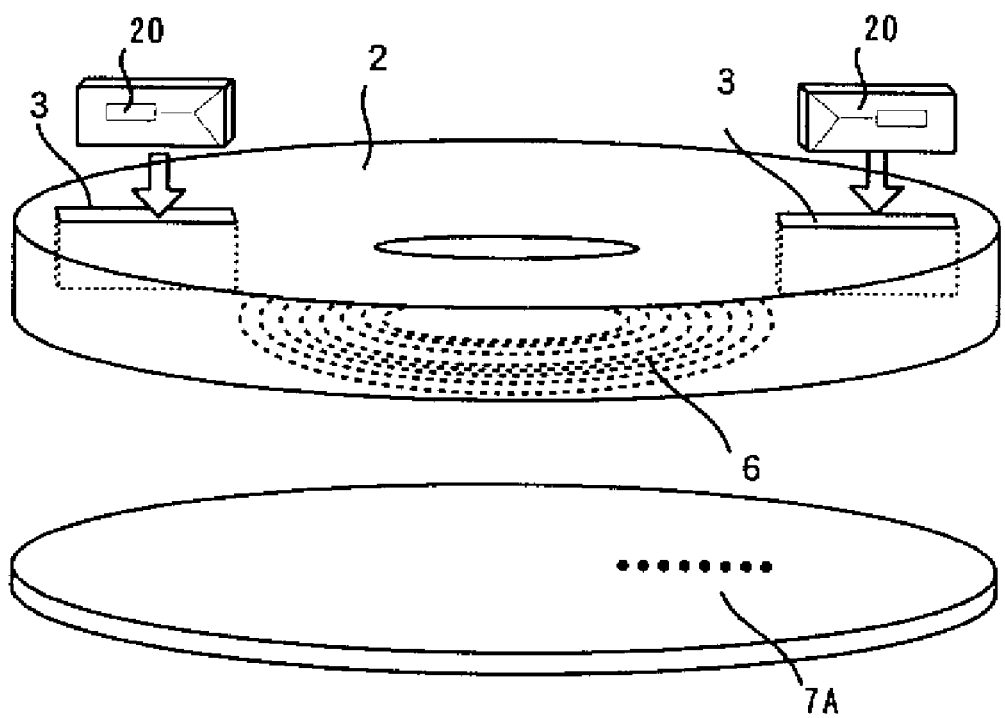
Figure 20A:
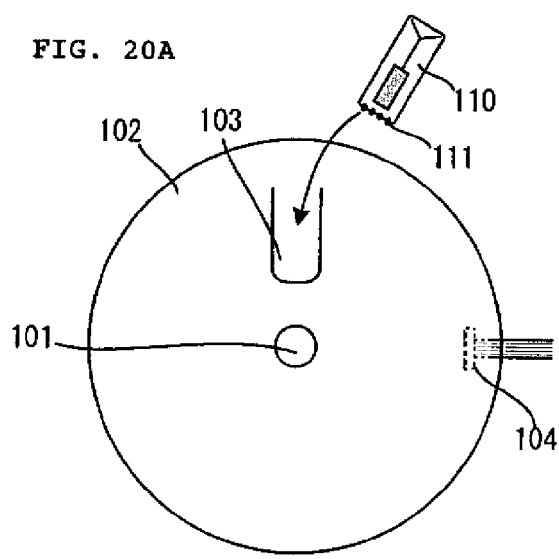
FIG. 20A to FIG. 20D are illustrations to explain a positional relationship between the contact for measurement and the electrode of the biosensor according to a conventional measuring apparatus utilizing centrifugal force.
Figure 20B:
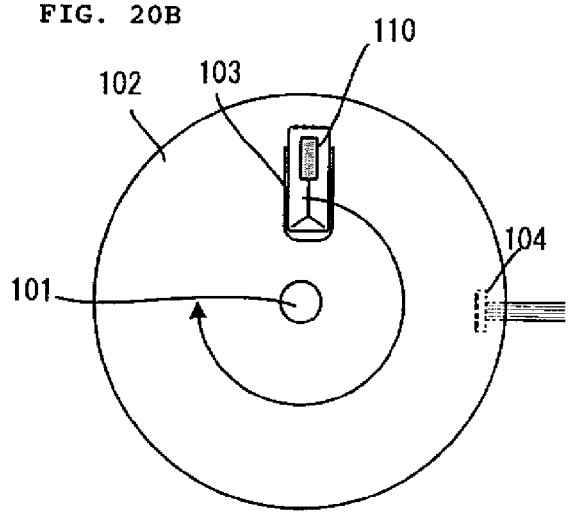
Figure 20C:
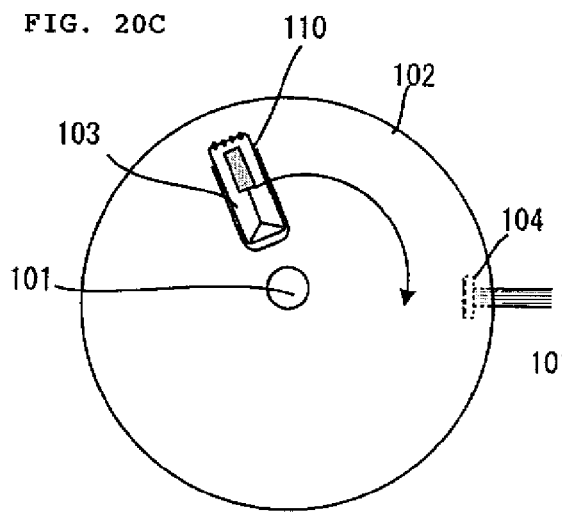
Figure 20D:
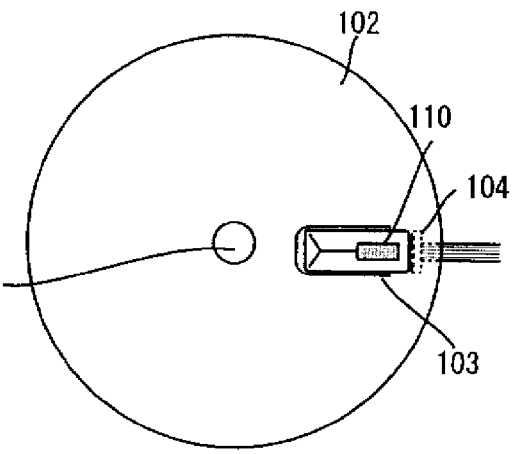

FIG. 19A and FIG. 19B are illustrations to explain a configuration to arrange multiple biosensors on the rotary table. FIG. 19A shows a configuration example in which two retainers 3 are provided at diametrically opposed locations to each other across the rotary shaft in the configuration example as shown in FIG. 1, and two biosensors are mounted thereon. FIG. 19B shows a configuration example in which two retainers 3 are provided at diametrically opposed locations to each other across the rotary shaft in the configuration example as shown in FIG. 13, and two biosensors are mounted thereon.

It is to be noted that in the examples above, two biosensors are mounted, but another configuration may be possible such as mounting a large number of biosensors, with an arrangement of a large number of retainers 3 on the rotary table 2.

According to the centrifugal measuring apparatus according to the present invention, a step of centrifugal separation and a step of measuring can be continuously performed with the biosensor being held on the rotary table. Furthermore, the measurement can be performed without aligning the rotary table after the step of centrifugal separation is finished.

What is claimed is:

1. A centrifugal measuring apparatus comprising a rotary table that is driven by both a motor and a rotor, a biosensor, a retainer that holds on the rotary table the biosensor accommodating a sample inside, an urged contact part that abuts against an electrode of the biosensor with a biased force to establish electrical connection, a measuring part that measures a signal from the electrode of the biosensor, and a connector part that selectively establishes the electrical connection between the urged contact part and the measuring part, wherein, either of the rotary table and the rotor being coaxial with the rotary table has a circular contact along a circumference of a rotary shaft, the circular contact being electrically connected to the urged contact part, the connector part comprises a movable contact that freely comes into contact with and separates from the circular contact at any position on a circle of the circular contact, when the rotary table is rotated, the connector part makes the movable contact to be separated from the circular contact, and centrifugal force generated by rotating the rotary table is applied to the sample within the biosensor, and when the rotary table is stopped, the connector part makes the movable contact and the circular contact to be in contact with each other, and electrical connection between the biosensor and the measuring part is established via the connector part.

2. The centrifugal measuring apparatus according to claim 1, wherein,
    a plurality of the circular contacts are placed respectively at different positions in the axial direction, on an outer circumference surface or an inner circumference surface of either of a cylindrical body and a cone that is provided coaxially with the rotary table.

3. The centrifugal measuring apparatus according to claim 1, wherein,
    a plurality of the circular contacts are placed concentrically with different diameters on a board face of the rotary table.

4. The centrifugal measuring apparatus according to claim 2, wherein,
    the urged contact and the circular contact are electrically connected by wiring placed on the rotary table.

5. The centrifugal measuring apparatus according to claim 1, wherein,
    the movable contact comprises,
    an elastic contact and
    a moving mechanism that enables the elastic contact to be moved freely towards the circular contact.

6. A centrifugal measuring apparatus comprising, a rotary table that is driven by a motor, a biosensor, a retainer that holds on the rotary table the biosensor accommodating a sample inside, an urged contact part that abuts against an electrode of the biosensor with a biased force to establish electrical connection, a measuring part that measures a signal from the electrode of the biosensor, and a connector part that selectively establishes the electrical connection between the urged contact and the measuring part, wherein, the rotary table has a point of contact on a circle along a circumference of a rotary shaft, the point of contact being electrically connected with the urged contact, the connector part has a circular movable contact that freely comes into contact with and separates from the point of contact on the rotary table, at any circular position, when the rotary table is rotated, the connector part makes the circular movable contact to be separated from the point of contact, and centrifugal force generated by rotating the rotary table subjects the sample within the biosensor to a centrifugal separation, and when the rotary table is stopped, the connector part makes the circular movable contact to abut against the point of contact, whereby the electrode of the biosensor is energized and a measured signal is transmitted from the electrode to the measuring part.

7. The centrifugal measuring apparatus according to claim 6, wherein,
    a plurality of circular movable contacts are placed concentrically with different diameters on a face of an opposed member provided in such a manner as opposed to the rotary table and freely coming into contact therewith and separating therefrom.

8. The centrifugal measuring apparatus according to claim 6, wherein,
    the circular movable contact comprises a moving mechanism that is movable towards the point of contact.

9. The centrifugal measuring apparatus according to claim 6, wherein, the connector part energizes the electrode of the biosensor via a contact having a circular shape and transmits a measured signal from the electrode to the measuring part.

10. The centrifugal measuring apparatus according to claim 5, wherein,
the moving mechanism comprises a solenoid.

11. The centrifugal measuring apparatus according to claim 1, wherein,
the retainer comprises a concave part to store the biosensor on a board face of the rotary table, and the urged contact part is provided, either of on a bottom surface of the concave part and on a side surface of the concave part.

12. The centrifugal measuring apparatus according to claim 1, wherein,
the urged contact part comprises a contact pin that comes into contact with the electrode, and a spring that elastically urges the contact pin in a predetermined direction.

13. The centrifugal measuring apparatus according to claim 1, wherein,
the rotary table is driven by a DC motor.

14. The centrifugal measuring apparatus according to claim 3, wherein,
the urged contact and the circular contact are electrically connected by wiring placed on the rotary table.

15. The centrifugal measuring apparatus according to claim 7, wherein,
the circular movable contact comprises a moving mechanism that is movable towards the point of contact.

16. The centrifugal measuring apparatus according to claim 7, wherein,
the connector part energizes the electrode of the biosensor via a contact having a circular shape and transmits a measured signal from the electrode to the measuring part.

17. The centrifugal measuring apparatus according to claim 8, wherein,
the moving mechanism comprises a solenoid.

18. The centrifugal measuring apparatus according to claim 6, wherein,
the retainer comprises a concave part to store the biosensor on a board face of the rotary table, and the urged contact part is provided, either of on a bottom surface of the concave part and on a side surface of the concave part.

19. The centrifugal measuring apparatus according to claim 6, wherein,
the urged contact part comprises a contact pin that comes into contact with the electrode, and a spring that elastically urges the contact pin in a predetermined direction.

20. The centrifugal measuring apparatus according to claim 6, wherein,
the rotary table is driven by a DC motor.

* * * * *